United States Patent
Matsusaka et al.

(10) Patent No.: US 7,784,370 B2
(45) Date of Patent: Aug. 31, 2010

(54) POWDERY/GRANULAR MATERIAL FLOWABILITY EVALUATION APPARATUS AND METHOD

(75) Inventors: Shuji Matsusaka, Kyoto (JP); Hiroaki Masuda, Nishinomiya (JP); Yanbin Jiang, Guangzhou (CN); Masatoshi Yasuda, Ikoma (JP)

(73) Assignee: Kyoto University (JP)

( * ) Notice: Subject to any disclaimer, the term of this patent is extended or adjusted under 35 U.S.C. 154(b) by 392 days.

(21) Appl. No.: 11/918,901

(22) PCT Filed: Apr. 19, 2006

(86) PCT No.: PCT/JP2006/308223

§ 371 (c)(1),
(2), (4) Date: Oct. 19, 2007

(87) PCT Pub. No.: WO2006/115145

PCT Pub. Date: Nov. 2, 2006

(65) Prior Publication Data

US 2009/0078029 A1   Mar. 26, 2009

(30) Foreign Application Priority Data

Apr. 21, 2005 (JP) .............................. 2005-123496
Jan. 10, 2006 (JP) .............................. 2006-002518

(51) Int. Cl.
*G01N 11/02* (2006.01)
(52) U.S. Cl. ....................................... 73/866
(58) Field of Classification Search ............ 73/866
See application file for complete search history.

(56) References Cited

U.S. PATENT DOCUMENTS 3,265,679 A * 8/1966 Black, III et al. ........... 428/402

(Continued)

FOREIGN PATENT DOCUMENTS

JP 5-249021 9/1993

(Continued)

OTHER PUBLICATIONS

Shuji Matsusaka et al.—"Shindo Mosaikekkan ni yoru Bifuntai no Biryo Teiryo Kyokyu"—Chemical Engineering, 1996, vol. 41, No. 10, pp. 24-31.

(Continued)

*Primary Examiner*—Thomas P Noland
(74) *Attorney, Agent, or Firm*—Gerald E. Hespos; Michael J. Porco

(57) ABSTRACT

A powdery/granular material flowability evaluation apparatus and a powdery/granular material flowability evaluation method are provided to evaluate the flowability of a powdery/granular material in a dynamic state of the powdery/granular material. The powdery/granular material flowability evaluation apparatus (A) has a hopper (111) for storing a powdery/granular material to be measured, a vertical tube (11) having a flow-in port (1121) connected with a discharge port (1112) of the hopper (111) through which the powdery/granular material is discharged, a vibrator (2) for giving vibration to the tube (11), a laser vibrometer (3) for measuring the amplitude of the tube (11), an electric balance (4) for measuring the weight of the powdery/granular material fallen through the tube 11 from the hopper (111), and an evaluation value calculating section (512) for calculating an evaluation value evaluating the flowability of the powdery/granular material based on the measured amplitude and weight.

11 Claims, 11 Drawing Sheets

U.S. PATENT DOCUMENTS 7,615,098 B2 * 11/2009 Brent et al. ............... 73/866 X

FOREIGN PATENT DOCUMENTS

| JP | 6-229901 | 8/1994 |
| --- | --- | --- |
| JP | 2000-74811 | 3/2000 |
| JP | 2001-74629 | 3/2001 |
| JP | 2002-162329 | 6/2002 |

OTHER PUBLICATIONS

Shuji Matsusaka, et al.—Micro-feeding of fine powders using a capillary tube with ultrasonic vibration, Advanced Powder Technol., 1995, vol. 6, No. 4, pp. 283-293.

* cited by examiner

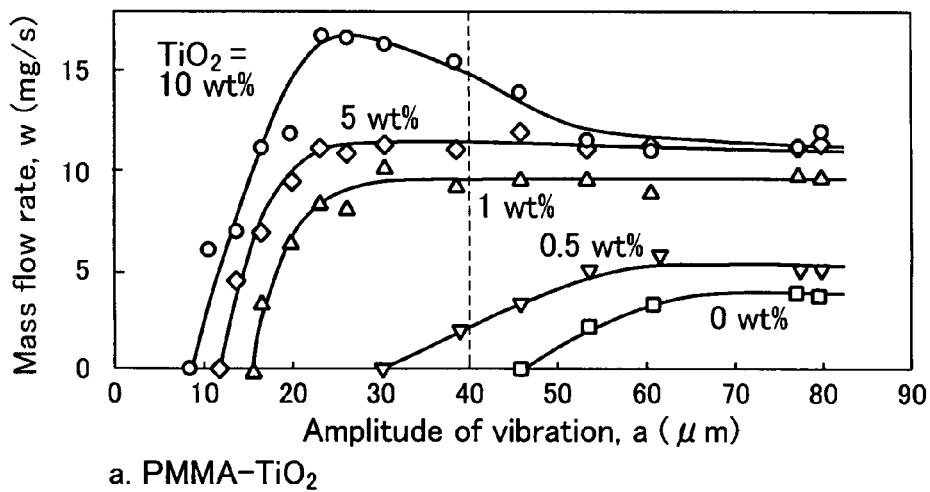
a. PMMA-TiO$_2$
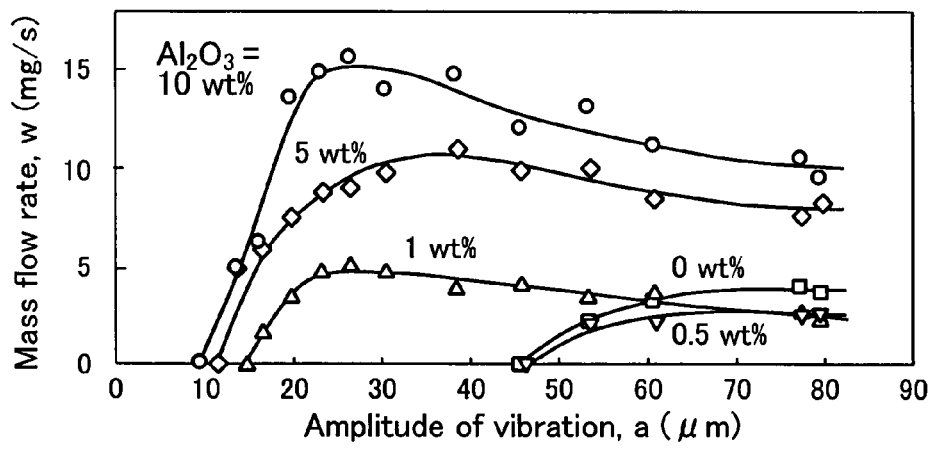
b. PMMA-Al$_2$O$_3$
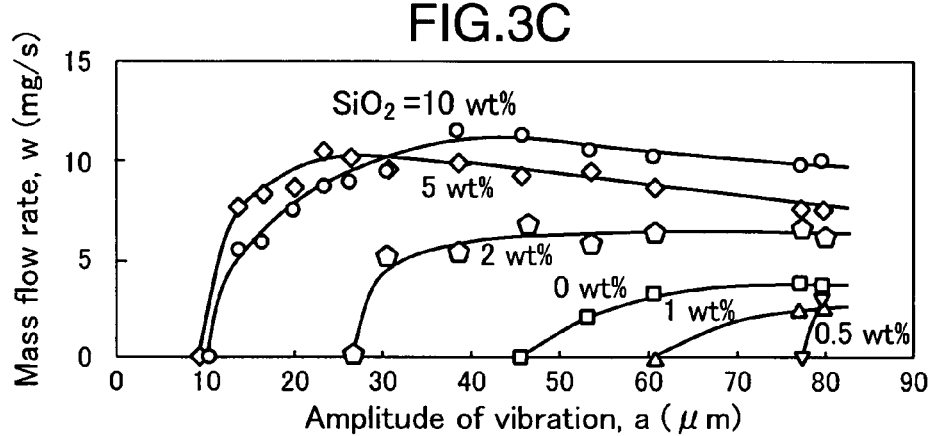
c. PMMA-SiO$_2$
(f=400Hz)

POWDERY/GRANULAR MATERIAL FLOWABILITY EVALUATION APPARATUS AND METHOD

TECHNICAL FIELD

The present invention relates to powdery/granular material flowability evaluation apparatus and method capable of relatively evaluating powdery/granular material flowability.

DESCRIPTION OF THE BACKGROUND ART

Powdery/granular material flowability is evaluated, for example, by measuring an angle of repose, a degree of compaction or a degree of aggregation. For example, an index value used to evaluate flowability is calculated by the Carr method and evaluated.

A method for measuring an angle of repose, which method is utilized upon evaluating such flowability, is disclosed, for example, in patent literature 1. This patent literature 1 discloses a method for measuring an angle of repose of a wet powdery/granular material using an apparatus including, from the top, a mesh screen, vibrating means for vibrating the mesh screen, a powdery/granular material sample pouring funnel, a table used to measure the angle of repose, and a support for supporting the vibrating means and the sample pouring funnel and particularly a method for measuring an angle of repose of a wet powdery/granular material, wherein the liquid content of the powdery/granular material sample lies within a range of 10 to 60 weight %, the mesh size of the screen mesh is 710 to 5600 μm, and the diameter of the bottom orifice of the sample pouring funnel lies within a range of 5 to 15 mm.

Further, the Japanese Industrial Standards JIS Z 2502 (2000) or ISO 4490 specifies a "Metallic Powdery/Granular Material—Flowability Testing Method". This "Metallic Powdery/Granular Material—Flowability Testing Method" is roughly a method for measuring a time required for 50 g of a metallic powdery/granular material to flow through an orifice of a calibrated funnel (Hall flowmeter) of a standard size by means of a stop watch and measuring the flowability of the metallic powdery/granular material based on this time.

The evaluation method according to the background art is for evaluating the flowability of the powdery/granular material from the angle of repose, degree of compaction and degree of aggregation that are measured in a stationary state of the powdery/granular material, but not for measuring the flowability of the powdery/granular material in a dynamic state of the powdery/granular material. Thus, evaluations by the evaluation method according to the background art could not be said to precisely reflect the flowability of the powdery/granular material in some cases.

Further, since a test is conducted as described above according to the "Metallic Powdery/Granular Material—Flowability Testing Method", there is an inconvenience that the powdery/granular material to be measured is limited to a metallic powdery/granular material naturally discharged by the action of gravity. The above "Metallic Powdery/Granular Material—Flowability Testing Method" cannot be applied, particularly, to adhesive powdery/granular materials.

[Patent Literature 1]

Japanese Unexamined Patent Publication No. 2002-162329

DISCLOSURE OF THE INVENTION

In view of the above situation, an object of the present invention is to provide powdery/granular material flowability evaluation apparatus and method capable of evaluating the flowability of a powdery/granular material in a dynamic state where the powdery/granular material itself is flowing or is about to start flowing.

The present inventors found out as a result of various studies that a starting point of the flow and a flow rate per unit time of a powdery/granular material flowing in a vibrating tube change depending on the amplitude of the tube.

A powdery/granular material flowability evaluation apparatus according to one aspect of the present invention gives vibration to an accommodating member accommodating a powdery/granular material and calculates an evaluation value evaluating the flowability of the powdery/granular material based on the amplitude of the given vibration and the weight of the powdery/granular material having come out of the accommodating member by giving the vibration. According to a powdery/granular material flowability evaluation method according to another aspect of the present invention, vibration is first given to an accommodating member accommodating a powdery/granular material and subsequently an evaluation value evaluating the flowability of the powdery/granular material is calculated based on the amplitude of the given vibration and the weight of the powdery/granular material having come out of the accommodating member by the given vibration.

It should be noted that the amplitude is related by an equation: (amplitude)=(acceleration of vibration)/$(2 \times \pi \times (\text{frequency}))^2$. The amplitude is proportional to the acceleration of the vibration if the frequency is constant.

The powdery/granular material flowability evaluation apparatus and powdery/granular material flowability evaluation method having such a construction can evaluate the flowability of the powdery/granular material in a dynamic state where the powdery/granular material itself is flowing or is about to start flowing.

BEST MODES FOR EMBODYING THE INVENTION

Figure 1:
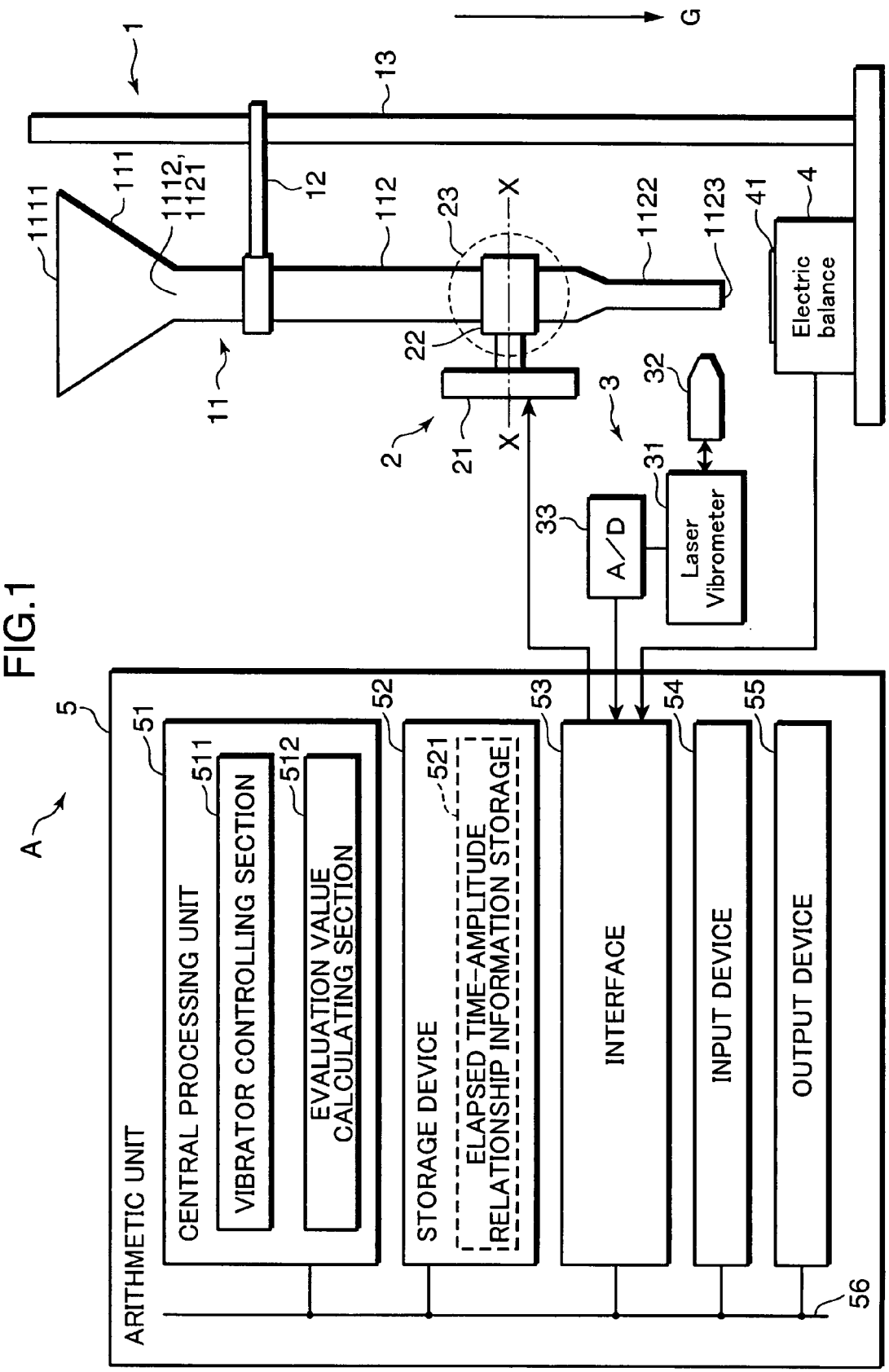
FIG. 1 is a diagram showing the construction of a powdery/granular material flowability evaluation apparatus according to one embodiment.

Hereinafter, one embodiment of the present invention is described with reference to the drawings. It should be noted that constructions identified by the same reference numerals in the respective figures are identical constructions and are not repeatedly described.

Construction of the Embodiment

FIG. 1 is a diagram showing the construction of a powdery/granular material flowability evaluation apparatus according to the embodiment. The powdery/granular material flowability evaluation apparatus A is an apparatus for giving vibration to an accommodating member accommodating a powdery/granular material and calculating an evaluation value evaluating the flowability of the powdery/granular material based on the amplitude of the given vibration and the weight of the powdery/granular material flown out from the accommodating member by this given vibration, and is provided with a powdery/granular material flowing unit 1, a vibrator 2, a laser vibrometer 3, an electric balance 4 and an arithmetic unit 5 as shown in FIG. 1.

The powdery/granular material flowing unit 1 includes a tube 11, a horizontal rod 12 supporting the tube 11 vertically (in other words, substantially in parallel with a direction G in which gravity acts), and a stand 13 for supporting the horizontal rod 12.

The tube 11 is an accommodating member for accommodating a powdery/granular material and comprised of a hopper part 111 for storing the powdery/granular material to be evaluated and a tube part 112 through which the powdery/granular material flows. The hopper part 111 is formed at its upper end with a throw-in port 1111 to enable the powdery/granular material to be poured thereinto, and is funnel-shaped to gradually reduce the diameter from the throw-in port 1111 to a discharge port 1112 so that the stored powdery/granular material can smoothly flow to the discharge port 1112 to be discharged. The tube part 112 has an flow-in port 1121 at the upper end connected with the discharge port 1112 of the hopper part 111 and is formed with a narrower tube portion 1122 having a smaller inner diameter at the bottom end. The tube 11 is supported on the horizontal rod 12 at the upper end of the tube part 112.

The inner diameter of the narrower tube portion 1122 is equivalent to a diameter at which the flowability of the powdery/granular material is desired to be evaluated, and is suitably set according to the material, size, adhesiveness and the like of the powdery/granular material passing the tube part 112. The outer diameter of the tube part 112 (i.e. thickness of the tube part 112) is suitably set to have such strength that the tube 11 is not broken when vibration is given from the vibrator 2 with the tube 11 supported on the horizontal rod 12. The length of the tube part 112 is not particularly limited as long as the vibration by the vibrator 2 is transmitted to the entire tube 11, but is preferably about several hundreds mm in view of the miniaturization of the apparatus. The tube 11 is made of a material having such rigidity that the vibration by the vibrator 2 is transmitted to the entire tube 11, e.g. glass or metal (e.g. steel or copper).

Although the tube 11 is vertically arranged so that gravity maximally acts on the powdery/granular material in this embodiment, it may be obliquely arranged at a specified angle to vertical direction since it is sufficient that gravity acts on the powdery/granular material.

The hopper part 111 is an example of a storage tank as claimed, and the tube part 112 is an example of a tube as claimed. In this embodiment, the storage tank and the tube as claimed are integrally formed as described above.

The vibrator 2 is an apparatus for giving vibration to the tube 11 as an example of the accommodating member at specified frequency and amplitude in accordance with a control signal from the arithmetic unit 5, and includes a vibrator main body 21 for generating vibration and a vibration transmitting member 22 for transmitting the vibration generated in the vibrator main body 21. The vibrator main body 21 is, for example, an electromagnetic vibrator for vibrating a vibrating plate connected to a movable coil disposed in a direct-current magnetic field produced by a permanent magnet or an exciting coil by supplying an alternating current to the movable coil; an electrostatic vibrator for vibrating a vibrating plate by forming a capacitor by a fixed electrode plate and the vibrating plate and supplying a voltage, in which an alternating-current voltage is superimposed on a direct-current bias voltage, to the fixed electrode plate and the vibrating plate; an electrostrictive vibrator for vibrating a vibrating plate by applying an alternating-current voltage to an electrostrictive element that is deformed upon the application of a voltage; or a vibration motor for generating vibration by rotating an eccentric weight attached to a rotary shaft of the motor. For example, the vibrator main body 21 may be a piezoelectric acoustic vibrator including a piezoelectric element. Since the amplitude and frequency (number of vibration) of the vibration can be independently controlled in the piezoelectric acoustic vibrator, there is an advantage of easily continuously changing the amplitude with the frequency fixed to a specified frequency set beforehand. Such a piezoelectric acoustic vibrator includes, for example, a donut-shaped piezoelectric element having a pair of facing electrodes on the opposite surfaces thereof and a metallic round piezoelectric vibrating plate, wherein the piezoelectric element is concentrically secured to one surface of the piezoelectric vibrating plate. In the piezoelectric acoustic vibrator having such a construction, when voltages are applied to the pair of facing electrodes, the piezoelectric vibrating plate neither elongates nor contracts while the piezoelectric element elongates or contracts in a radial direction according to the polarity of the voltages, wherefore the piezoelectric vibrating plate is warped upward or downward in a normal direction to the piezoelectric vibrating plate as the piezoelectric element elongates or contracts. Thus, these upward and downward warps are alternately repeated by applying the alternating-current voltages to the pair of facing electrodes and the piezoelectric vibrating plate vibrates. In this embodiment, an electromagnetic vibrator or a piezoelectric acoustic vibrator is used as the vibrator 2. The vibration transmitting member 22 is connected with the bottom end of the tube part 112 at a side toward the narrower tube portion 1122 to transmit vibration generated in the vibrator main body 21 to the tube 11. It should be noted that the vibrator 2 may be an ultrasonic vibration apparatus constructed to generate an ultrasonic wave and vibrate the tube 11 by irradiating this generated ultrasonic wave to the bottom end of the tube part 112. The vibrator 2 is an example of a vibrator unit as claimed.

The laser vibrometer 3 is an apparatus for measuring the amplitude of the tube 11 and outputting the measured amplitude to the arithmetic unit 5 and includes, for example, a laser vibrometer main body 31, a probe 32 and an analog/digital converter (hereinafter, abbreviated as "A/D") 33 for converting an analog signal into a digital signal. The laser vibrometer main body 31 causes the probe 32 to irradiate a laser beam to the narrower tube portion 1122 in the vicinity of a flow-out port 1123 and to receive the reflected light, calculates the amplitude by the laser Doppler method based on a laser beam irradiation timing and a light receiving timing at specified sampling intervals (e.g. every second) set beforehand, and outputs the calculation result to the arithmetic unit 5 via the A/D 33. Since the vicinity of the flow-out port 1123 of the tube 11 where the powdery/granular material flows out is an open end of the vibration in this embodiment, the laser vibrometer 3 is so arranged as to measure the amplitude of the narrower tube portion 1122 in the vicinity of the flow-out port 1123 of the tube 11 and output the measurement result to the arithmetic unit 5 in this way. The laser vibrometer 3 is an example of an amplitude meter as claimed.

The electric balance 4 is an apparatus for measuring the weight of the powdery/granular material fallen through the tube part 112 from the hopper part 111 and outputting the measured weight to the arithmetic unit 5. In the electric balance 4, a weighing platform 41 on which an object to be weight-measured is placed is disposed below the flow-out port 1123 of the tube 11. The electric balance 4 receives the powdery/granular material falling from the tube part 11 with the weighing platform 41, measures the weight of the powdery/granular material at the specified sampling intervals (e.g. every second) set beforehand, and digitally outputs the measured weight to the arithmetic unit 5. The detection sensitivity of the electric balance 4 is suitably determined according to an average weight of one particle of the powdery/granular material and accuracy required for the evaluation value to be calculated, and is 0.1 mg in this embodiment. The electric balance 4 is an example of a weight meter as claimed.

The arithmetic unit 5 is a unit for controlling the frequency and amplitude of the vibration generated by the vibrator 2 and calculating the evaluation value evaluating the flowability of the powdery/granular material based on the amplitude measured by the laser vibrometer 3 and the weight measured by the electric balance 4 in a dynamic state of the powdery/granular material.

The arithmetic unit 5 includes, for example, a central processor 51, a storage device 52, an interface 53, an input device 54, an output device 55 and a bus 56.

The interface 53 is an interface circuit for connecting the arithmetic unit 5 and an external apparatus in such a manner as to enable data input and output therebetween. The interface 53 converts a control signal from the central processor 51 into a data of such a format processable by the vibrator 2, and converts data from the laser vibrometer 3 and electric balance 4 into data of such a format processable by the central processor 51. The input device 54 is a device for inputting various commands such as a start command instructing the start of the measurement of the evaluation value and various data such as a value of the frequency of the vibration generated by the vibrator 2 to the arithmetic unit 5 and is, for example, a keyboard, a mouse or the like. The output device 55 is a device for outputting commands and data inputted from the input device 54, the evaluation value of the powdery/granular material and the like and is, for example, a display device such as a CRT display, an LCD, an organic EL display or a plasma display or a printing device such as a printer.

The storage device 52 is for storing various programs such as a control program for controlling the powdery/granular material flowability evaluation apparatus A and data generated during the execution of the various programs. The storage device 52 includes, for example, a volatile storage element such as a RAM (Random Access Memory) serving as a so-called working memory of the central processor 51 and nonvolatile storage elements such as a ROM (Read Only Memory) and a rewritable EEPROM (Electrically Erasable Programmable Read Only Memory).

The central processor 51 includes, for example, a microprocessor, its peripheral circuits and the like, is functionally provided with a vibrator controlling section 511 for controlling the vibrator 2 to generate the vibration of specified frequency and amplitude and an evaluation value calculating section 512 for calculating the evaluation value evaluating the flowability of the powdery/granular material based on the amplitude measured by the laser vibrometer 3 and the weight measured by the electric balance 4, and controls the storage device 52, interface 53, input device 54 and output device 55 according to these functions in accordance with the control program and further controls the vibrator 2 via the interface 53.

These central processor 51, storage device 52, interface 53, input device 54 and output device 55 are connected by the bus 56 so as to exchange data to each other.

Such an arithmetic unit 5 can be, for example, constructed by a computer, more specifically by a notebook or desktop personal computer.

The arithmetic unit 5 may further include an external storage device (not shown) according to needs. The external storage device is a device for reading and/or writing data in and from recording media such as flexible discs, CD-ROMs (Compact Disc Read Only Memories), CD-Rs (Compact Disc Recordables) or DVD-Rs (Digital Versatile Disc Recordables) and is, for example, a flexible disc drive, a CD-ROM drive, a CD-R drive, a DVD-R drive or the like.

Next, the operation of this embodiment is described.

Operation of the Embodiment

In the case of measuring an evaluation value on the flowability of a powdery/granular material, a measurer first determines a frequency (cycle) suited to measuring vibration given to the tube 11 by the vibrator 2. This is because the frequency characteristic of the tube 11 connected with the vibrator 2 and supported by the horizontal rod 12 differs depending on the powdery/granular material passing through the tube 11 to be measured. Thus, the frequency of the vibration given to the tube 11 needs to be determined according to the powdery/granular material to be measured.

Upon determining this frequency, the measurer starts the arithmetic unit 5, the laser vibrometer 3 and the electric balance 4 and throws the powdery/granular material to be measured into the hopper part 111 of the tube 11 through the throw-in port 1111, thereby preparing for a measurement. Then, the measurer measures the amplitude of the tube 11 while changing the frequency of the vibration given to the tube 11 (frequency of the vibrator 2) within a specified range.

Figure 2:
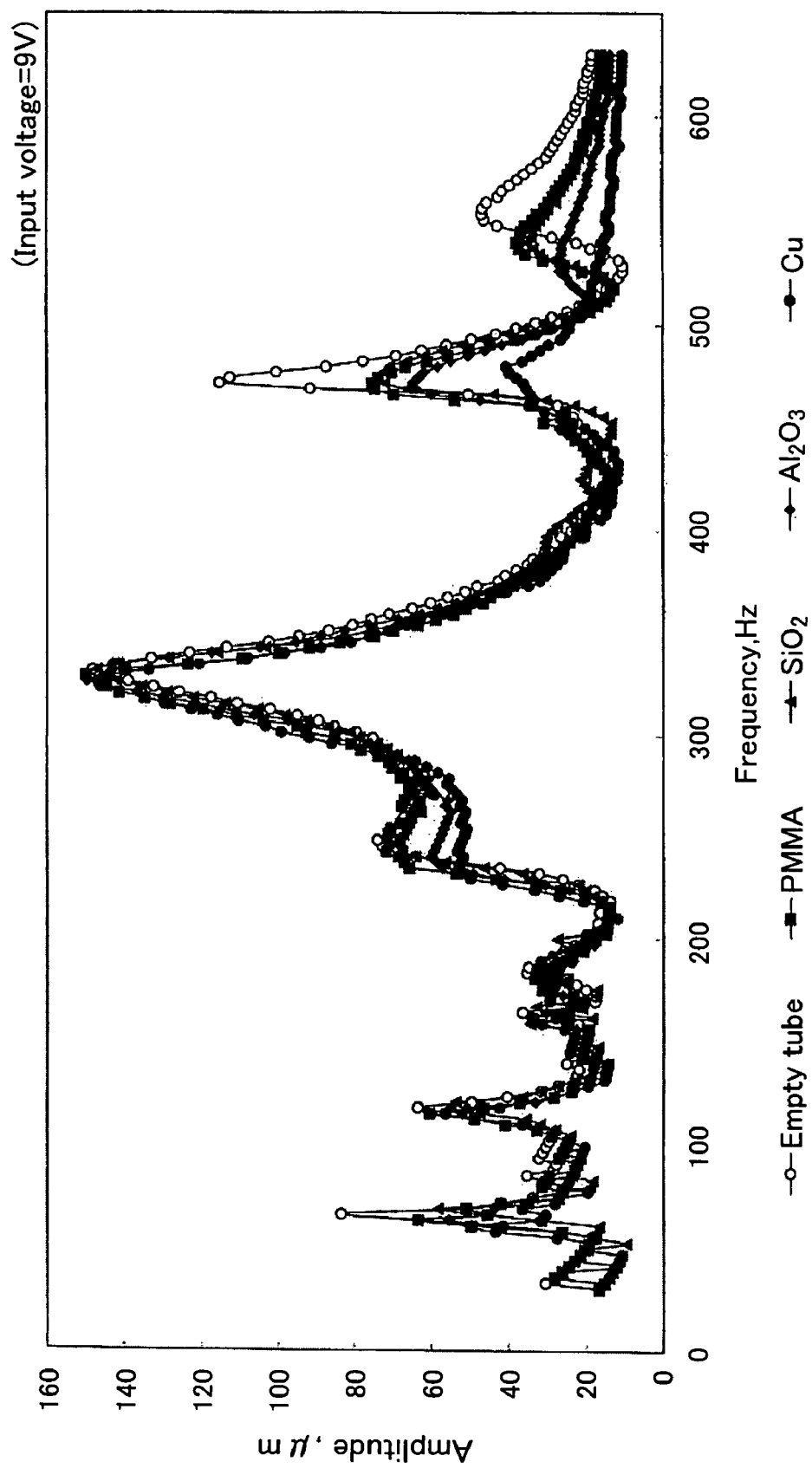
FIG. 2 is a graph showing a frequency characteristic of a tube, FIG. 3 are graphs showing a flow rate per unit time in relation to amplitude.

As examples, frequency characteristics of the tube 11 made of glass for powdery/granular materials of polymethylmetacrylate, silicon oxide, aluminum oxide and copper having an average particle diameter of about 10 μm are shown in FIG. 2. This glass tube 11 is such that the inner diameter of the tube part 112 is about 6 mm, that of the narrower tube portion 1122 at the bottom end of the tube part 112 is about 1.2 mm and the entire length of the tube part 112 is about 150 mm with its bottom side of about 50 mm allotted as the narrower tube portion 1122. Further, the amplitude of the narrower tube portion 1122 in the vicinity of the flow-out port 1123 was measured as the amplitude of the tube 11.

FIG. 2 is a graph showing the frequency characteristics of the tube, wherein a horizontal axis represents frequency in Hz and a vertical axis represent amplitude in μm. ○ represents measurement values in the case where the powdery/granular material was not passed through the tube 11. ■ represents measurement values in the case where PMMA (polymethyl-metacrylate) was passed as the powdery/granular material through the tube 11. ▲ measurement values in the case where $SiO_s$ (silicon oxide) was passed as the powdery/granular material through the tube 11. ♦ measurement values in the case where $Al_2O_3$ (aluminum oxide) was passed as the powdery/granular material through the tube 11. ● measurement values in the case where Cu (copper) passed was as the powdery/granular material through the tube 11.

As can be understood from FIG. 2, the respective frequency characteristics of the tube 11 differed in the case where the powdery/granular material was passed through the tube 11 and in the case where no powdery/granular material was passed through the tube 11, and in the case where the material of the powdery/granular material was changed. The respective frequency characteristics differ in this way, but have such a profile that a first order resonance appears at about 330 Hz and higher order resonances appear before and after this frequency in the tube 11 having the above dimensions.

In the measurement of the evaluation value of the powdery/granular material according to the present invention, the vibrator 2 needs to be driven at least at a frequency at which the tube 11 vibrates since the tube 11 needs to be vibrated. The application of vibration to the tube 11 at a resonance frequency is advantageous in view of power consumption, but is not preferable in view of measurement accuracy since the amplitude changes to a larger degree than a frequency change when the frequency changes. Therefore, in order to improve the measurement accuracy, it is preferable to measure at a frequency at which the amplitude changes a little even if the frequency changes.

Since a frequency range of about 250 Hz to about 300 Hz is the one within which the amplitude changes a little even if the frequency changes in the case of FIG. 2, a measurement frequency is preferably determined within this frequency range.

Further, in the case of measuring an evaluation value for one kind of powdery/granular material, it is sufficient to select a certain frequency from the frequency range as described above. However, in the case of measuring evaluation values for a plurality of kinds of powdery/granular materials without changing the measurement frequency, it is preferable to conduct measurements for the respective powdery/granular materials at such a frequency where the amplitude changes a little even if the frequency changes in order to conduct measurements with approximately the same measurement accuracy. In the case of FIG. 2, even if the frequency changes around about 300 Hz for the respective powdery/granular materials, the amplitude changes a little.

After the frequency of the vibration of the vibrator 2 is set, the evaluation value of the powdery/granular material to be measured is measured. The measurer first prepares for the measurement by starting the arithmetic unit 5, the laser vibrometer 3, and electric balance 4, setting the frequency of the vibration of the vibrator 2 in the arithmetic unit 5 and throwing the powdery/granular material to be measured into the hopper part 111 of the tube 11 through the throw-in port 1111. Then, the measurer instructs the start of the measurement to the arithmetic unit 5.

Upon receiving the instruction to start the measurement, the vibrator controlling section 511 in the central processor 51 of the arithmetic unit 5 causes the vibrator 2 to vibrate at specified frequency and amplitude only for a specified period, and the arithmetic unit 5 gives the vibration to the tube 11 by means of the vibrator 2. The laser vibrometer 3 measures the amplitude of the vibration of the tube 11 at the specified sampling intervals, and outputs the measured amplitudes of the tube 11 to the arithmetic unit 5. The electric balance 4 measures the weight of the fallen powdery/granular material at the specified sampling intervals, and outputs the measured weights of the powdery/granular material to the arithmetic unit 5. The evaluation value calculating section 512 in the central processor 51 of the arithmetic unit 5 stores the outputs from the laser vibrometer 3 and those from the electric balance 4 in the storage device 52 while relating them to each other.

Upon the lapse of a specified period, the arithmetic unit 5 causes the vibrator 2 to vibrate at the specified frequency and the next amplitude in order to conduct a measurement by causing the vibrator 2 to vibrate at the next amplitude, thereby giving vibration to the tube 11 by means of the vibrator 2. The laser vibrometer 3 measures the amplitude of the vibration of the tube 11 at the specified sampling intervals, and outputs the measured amplitudes of the tube 11 to the arithmetic unit 5. The electric balance 4 measures the weight of the fallen powdery/granular material at the specified sampling intervals, and outputs the measured weights of the powdery/granular material to the arithmetic unit 5. The evaluation value calculating section 512 in the central processor 51 of the arithmetic unit 5 stores the outputs from the laser vibrometer 3 and those from the electric balance 4 in the storage device 52 while relating them to each other.

Thereafter, the arithmetic unit 5 similarly obtains the outputs from the laser vibrometer 3 and those from the electric balance 4 and stores them in correspondence in the storage device 52 while successively increasing the amplitude of the vibration generated by the vibrator 2 at specified intervals within a specified range.

Upon completing the measurements of the amplitudes of the tube 11 corresponding to the respective amplitudes of the vibration generated by the vibrator 2 in the specified range and the weights of the fallen powdery/granular material, the evaluation value calculating section 512 in the central processor 51 of the arithmetic unit 5 generates a graph of a flow rate per unit time in relation to amplitude based on the outputs from the laser vibrometer 3 and those from the electric balance stored in the storage device 52, and outputs the generated graph to the output device 55. Since the amplitudes and weights are measured at the specified sampling intervals, the flow rate per unit time can be calculated by dividing a difference between the present weight and the previous weight by the time of the sampling interval. Particularly, if the sampling interval is set at 1 sec., the flow rate per second can be calculated by subtracting the previous weight from the present weight. Since the division processing can be omitted, a calculation time can be shortened.

The arithmetic unit 5 calculates a specified evaluation value based on the outputs from the laser vibrometer 3 and those from the electric balance 4 stored in the storage device 52, and outputs the calculated evaluation value to the output device 55. For example, the evaluation value is a flow rate per unit time of the powdery/granular material flowing in the tube 11 when the vibration is given to the tube 11 by the vibrator 2 so that the amplitude of the tube 11 (amplitude of the narrower tube portion 1122 in the vicinity of the flow-out port 1123 in this embodiment) has a specified level. The flow rates of the respective powdery/granular materials to be measured can be relatively evaluated by these evaluation values. The level of the amplitude is suitably set beforehand according to the powdery/granular material to be measured. For example, the evaluation value is the level of the amplitude of the tube 11 (amplitude of the narrower tube portion 1122 in the vicinity of the flow-out port 1123 in this embodiment) when the powdery/granular material fell from the tube 11. A timing at which the powdery/granular material fell from the tube 11 can be detected as a timing at which the electric balance 4 detected the weight. By these evaluation values, flow starting points of the respective powdery/granular materials to be measured can be relatively evaluated.

As an example, flow rates per unit time in relation to amplitude were measured using the tube 11 of the above respective dimensions for a polymethylmetacrylate powdery/granular material surface-treated with titanium oxide (hereinafter, abbreviated as "PMMA-$TiO_2$"), a polymethylmetacrylate powdery/granular material surface-treated with aluminum oxide (hereinafter, abbreviated as "PMMA-$Al_2O_3$") and a polymethylmetacrylate powdery/granular material surface-treated with silicon oxide (hereinafter, abbreviated as "PMMA-$SiO_2$"), each material having a particle diameter of about 10 μm. The amplitude of the narrower tube portion 1122 in the vicinity of the flow-out port 1123 was measured as the amplitude of the tube 11. Further, the frequency characteristics of the tube 11 were measured for the respective materials and the frequency of the vibration of the vibrator 2 was set at 400 Hz.

PMMA-$TiO_2$ is formed by fusing (mechanofusing) titanium oxide particles to the outer surfaces of polymethylmetacrylate particles. PMMA-$Al_2O_3$ is formed by fusing aluminum oxide particles to the outer surfaces of polymethylmetacrylate particles. PMMA-$SiO_2$ is formed by fusing polymethylmetacrylate powdery/granular material surface-treated with silicon oxide.

FIG. 3 are graphs showing flow rates per unit time in relation to amplitude, wherein a horizontal axis represents amplitude in μm and a vertical axis represent flow rate per unit time in mg/s.

FIG. 3A shows a measurement result of PMMA-$TiO_2$ when an amount of titanium oxide to be fused was changed to 0, 0.5, 1, 5 and 10 wt % (weight %). □ represents measurement values when the amount of titanium oxide was 0 wt %. ▽ represents measurement values when the amount of titanium oxide was 0.5 wt %. △ represents measurement values when the amount of titanium oxide was 1 wt %. ◇ represents measurement values when the amount of titanium oxide was 5 wt %. ○ represents measurement values when the amount of titanium oxide was 10 wt %.

FIG. 3B shows a measurement result of PMMA-$Al_2O_3$ when an amount of aluminum oxide to be fused was changed to 0, 0.5, 1, 5 and 10 wt % (weight %). □ represents measurement values when the amount of aluminum oxide was 0 wt %. ▽ represents measurement values when the amount of aluminum oxide was 0.5 wt %. △ represents measurement values when the amount of aluminum oxide was 1 wt %. ◇ represents measurement values when the amount of aluminum oxide was 5 wt %. ○ represents measurement values when the amount of aluminum oxide was 10 wt %.

FIG. 3C shows a measurement result of PMMA-$SiO_2$ when an amount of silicon oxide to be fused was changed to 0, 0.5, 1, 2, 5 and 10 wt % (weight %). □ represents measurement values when the amount of silicon oxide was 0 wt %. ▽ represents measurement values when the amount of silicon oxide was 0.5 wt %. △ represents measurement values when the amount of silicon oxide was 1 wt %. ◇ represents measurement values when the amount of silicon oxide was 5 wt %. ○ represents measurement values when the amount of silicon oxide was 10 wt %.

As can be understood from FIGS. 3A to 3C, the fall (flow) of the powdery/granular material starts at a certain level of the amplitude of the tube 11 and, thereafter, the flow rate per unit time in relation to amplitude roughly increases as the amplitude increases, maximizes at a certain amplitude of the tube 11 and decreases as the amplitude increases after the maximum flow rate is kept (saturated) or immediately after reaching the maximum flow rate in any of the cases of PMMA-$TiO_2$, PMMA-$Al_2O_3$ and PMMA-$SiO_2$.

The compressibility of the powdery/granular material is thought to concern the fact that the flow rate per unit time in relation to amplitude has such a profile.

Figure 4:
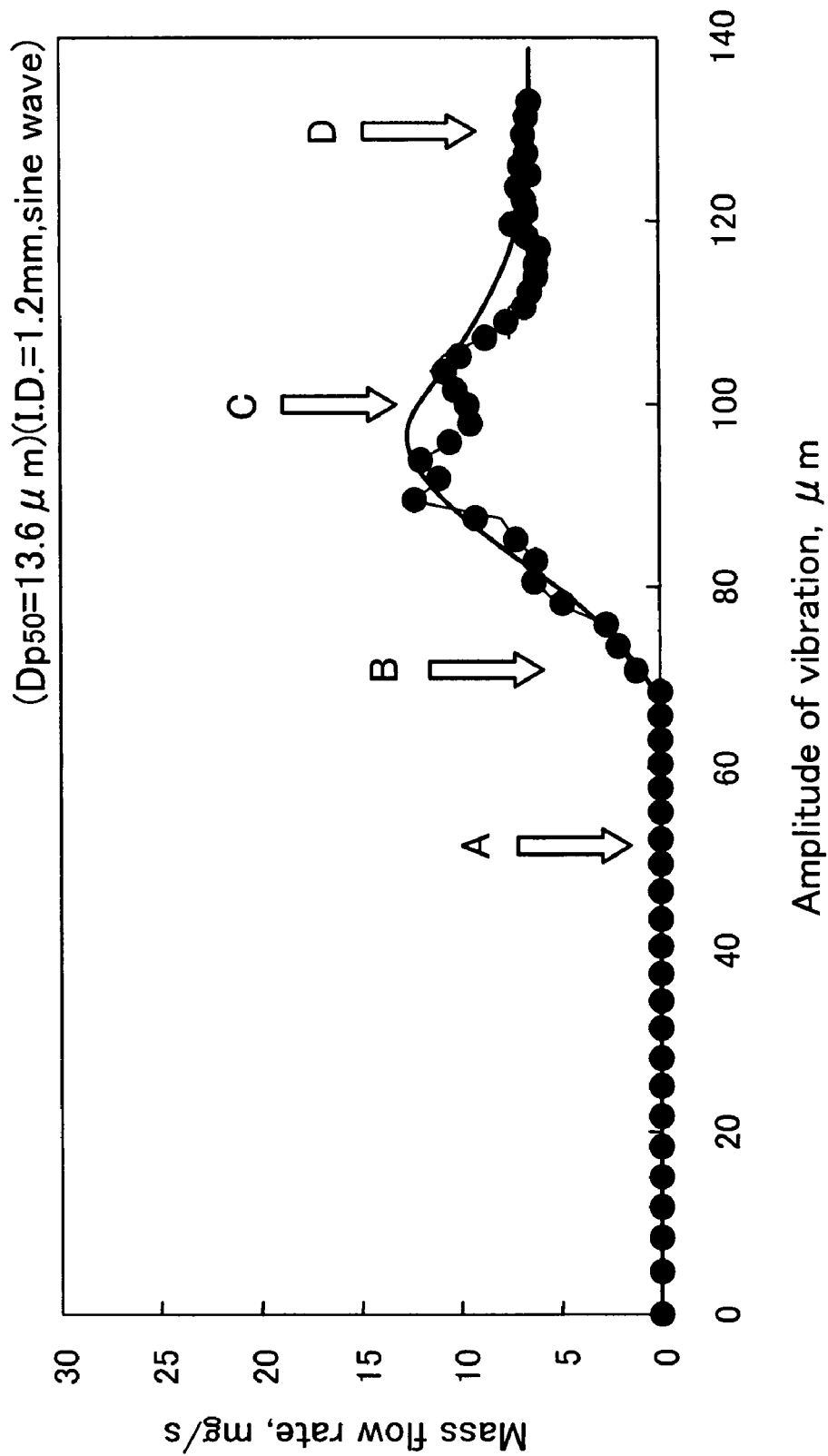
FIG. 4 is a graph showing the flow rate per unit time in relation to amplitude by continuous measurements, FIG. 5 are views showing CT scan images obtained by photographing the state of a powdery/granular material in the center of a narrower tube portion, FIG. 6 are graphs showing changes of the flow rate per unit time of the powdery/granular material with time in the case of specified amplitudes.
Figure 5:
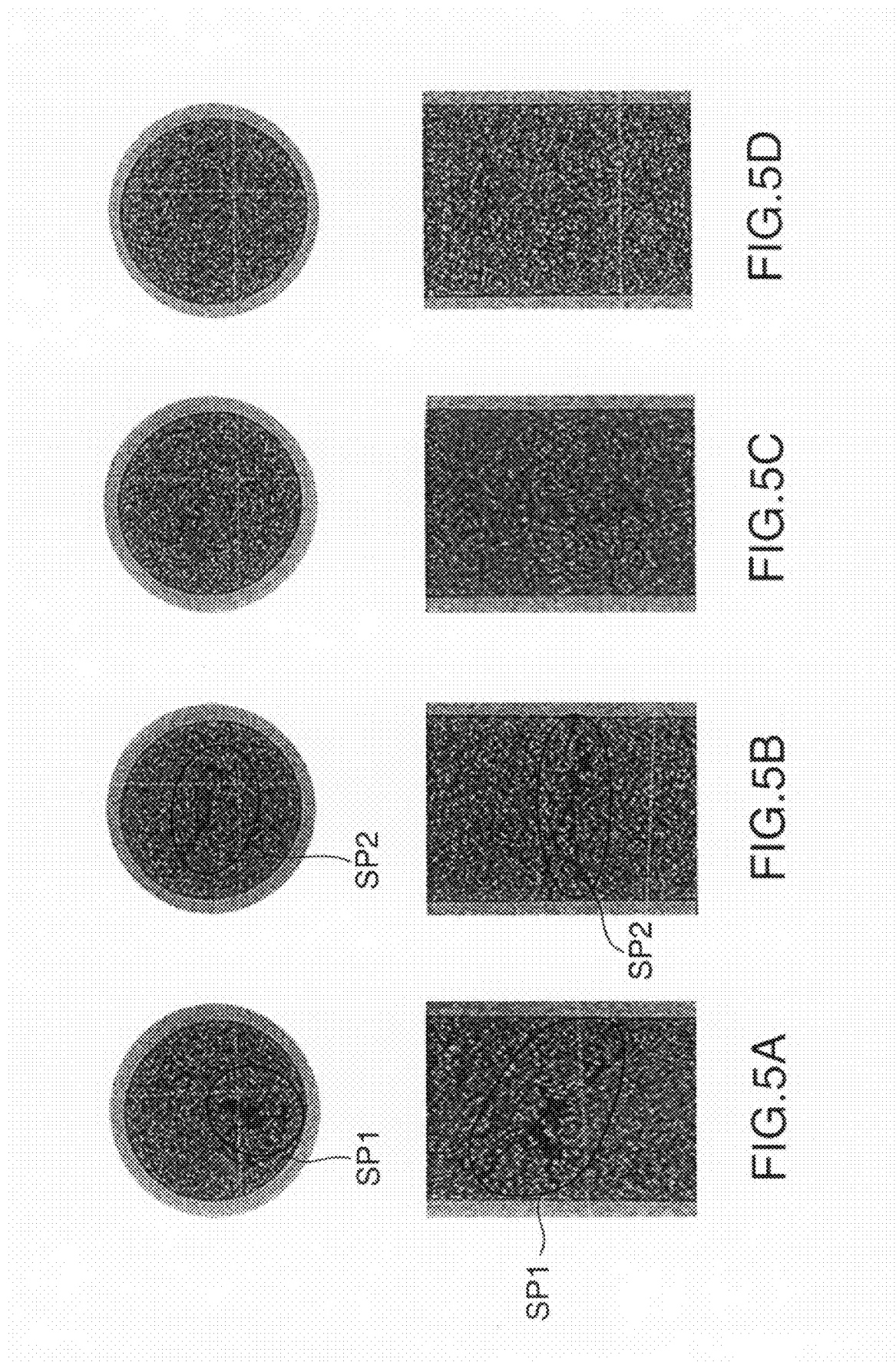

FIG. 4 is a graph showing the flow rate per unit time in relation to amplitude by continuous measurements. FIG. 5 are views showing CT scan images obtained by photographing the state of the powdery/granular material in the center of the narrower tube portion. In FIG. 4, a horizontal axis represents the amplitude in μm and a vertical axis represents the flow rate per unit time in mg/s. FIG. 4 shows a measurement result obtained by a measurement method to be described later for measurements made while the amplitude of the vibration given to the tube 11 by the vibrator 2 were continuously changed at a specified rate within a specified range. FIG. 5A shows a CT scan image in the narrower tube portion 1122 in a state where the powdery/granular material is not falling from the tube 11 although vibration is given to the tube 11 at an amplitude (about 50 μm) shown by an arrow A in FIG. 4. FIG. 5B shows a CT scan image in the narrower tube portion 1122 immediately after the fall (flow) of the powdery/granular material was started when vibration was given to the tube 11 at an amplitude (about 70 μm) shown by an arrow B in FIG. 4. FIG. 5C shows a CT scan image in the narrower tube portion 1122 in a state where the flow rate per unit time in relation to amplitude is maximized or in a state immediately after the maximized state when vibration was given to the tube 11 at an amplitude (about 100 μm) shown by an arrow C in FIG. 4. FIG. 5D shows a CT scan image in the narrower tube portion 1122 in a state where the flow rate per unit time in relation to amplitude decreases as the amplitude increase when vibration was given to the tube 11 at an amplitude (about 130 μm) shown by an arrow D in FIG. 4. In FIGS. 5A to 5D, upper views are horizontal sections of the central part of the narrower tube portion 1122 and lower views are vertical sections of the central part of the narrower tube portion 1122. Upon CT scanning, photographing is made with the vibration stopped when reaching the respective states. FIGS. 4 and 5 show the measurement result of $SiO_2$ having an average particle diameter of 13.6 μm in the case of vibration at a frequency of 330 Hz.

With the powdery/granular material to be measured thrown in through the throw-in port 1111, there are spaces (e.g. space SP1 shown in FIG. 5A) in spots in the tube 11 with a fairly rough density distribution of the powdery/granular material. Thus, even if it is started to give the vibration to the tube 11, the flow is hindered in spots where the powdery/granular material is dense while this vibration energy is consumed to reduce such spaces (spots where the density of the powdery/granular material is rough) in size. Therefore, even if it is started to give the vibration to the tube 11, a state where the powdery/granular material does not fall from the tube 11 continues for a while. When the amplitude is further increased, such spaces are reduced in size by the vibration and the rough density distribution of the powdery/granular material is loosened up. When such spaces reach a certain size, e.g. become a space SP2 of the size shown in FIG. 5B in the example shown in FIG. 4, the fall (flow) of the powdery/granular material starts. When the amplitude is further increased, such spaces are further reduced in size by the vibration and the rough density distribution of the powdery/granular material is more loosened up to make the powdery/granular material more uniform, thereby decreasing the dense spots hindering the flow of the powdery/granular material. Thus, the flow rate per unit time of the powdery/granular material also increases as the amplitude increases. Then, at a certain amplitude, particle intervals become suitable for the flow of the powdery/granular material as shown in FIG. 5C to maximize the flow rate per unit time of the powdery/granular material. When the amplitude is further increased, the particle intervals are narrowed to increase frictional forces between particles and frictional forces between the inner wall of the tube 11 and the particles. Therefore, the flow rate per unit time of the powdery/granular material decreases as the amplitude increases.

It is inferred that the aforementioned phenomenon occurs if the amplitude of the tube 11 is increased, and that there are an effect of improving the flowability of the powdery/granular material and simultaneously an effect of densely filling the powdery/granular material by applying external forces against the adherence and friction of the powdery/granular material to the powdery/granular material.

As described above, a characteristic curve of the flow rate per unit time in relation to amplitude represents flowability relating to the compressibility of the powdery/granular material. Not only depending on a difference in the flowability of the powdery/granular material, but also depending on a difference in the compressibility of the powdery/granular material, the value of the amplitude at which the flow of the powdery/granular material starts, the increasing rate of the flow rate per unit time in relation to the increasing rate of the amplitude, the maximum flow rate, the level of the amplitude to give the maximum flow rate, the amplitude range to give the maximum flow rate and the decreasing rate of the flow rate per unit time in relation to the increasing rate of the amplitude after reaching the maximum flow rate and the like differ, wherefore the characteristic curve takes on various shapes. The value of the amplitude at which the flow of the powdery/granular material starts, the increasing rate of the flow rate per unit time in relation to the increasing rate of the amplitude, the maximum flow rate, the level of the amplitude to give the maximum flow rate, the amplitude range to give the maximum flow rate and the decreasing rate of the flow rate per unit time in relation to the increasing rate of the amplitude after reaching the maximum flow rate, which characterize these characteristic curves, can be used as evaluation values for the flowability of the powdery/granular material.

As can be understood from FIGS. 3A to 3C, the amplitude of the tube 11 (amplitude when the flow rate per unit time=0 in FIG. 3) when the powdery/granular material fell from the tube 11 differs depending on an amount of the surface treating material ($TiO_2$, $Al_2O_3$ and $SiO_2$) in any of the cases of PMMA-$TiO_2$, PMMA-$Al_2O_3$ and PMMA-$SiO_2$. For example, in the case of PMMA-$TiO_2$ shown in FIG. 3A, the amplitude of the tube 11 when the powdery/granular material fell from the tube 11 was about 47 μm when the content of titanium oxide was 0 wt %, about 30 μm when the content of titanium oxide was 0.5 wt %, about 17 μm when the content of titanium oxide was 1 wt %, about 12 μm when the content of titanium oxide was 5 wt % and about 9 μm when the content of titanium oxide was 10 wt %. As a result, PMMA-$TiO_2$ can be understood to increase its flowability as the amount of $TiO_2$ fused to the outer surfaces increases. In this way, the amplitude of the tube 11 when the powdery/granular material fell from the tube 11 can be used as the evaluation value for the flowability of the powdery/granular material. Of course, this evaluation value for the flowability is also a value relating to the compressibility of the powdery/granular material as described above and can be used as an evaluation value for the compressibility if the compressibility of the powdery/granular material is a main viewpoint.

As can be further understood from FIGS. 3A to 3C, the flow rate per unit time of the powdery/granular material flowing in the tube 11 in the case where vibration is given to the tube 11 by the vibrator 2 so that the amplitude of the tube 11 (amplitude of the narrower tube portion 1122 in the vicinity of the flow-out port 1123 in this embodiment) has a specified level differs depending on an amount of the surface treating material ($TiO_2$, $Al_2O_3$ and $SiO_2$) in any of the cases of PMMA-$TiO_2$, PMMA-$Al_2O_3$ and PMMA-$SiO_2$. For example, in the case of PMMA-$TiO_2$ shown in FIG. 3A and the amplitude of the tube 11 of 40 μm, the flow rate per unit time of the powdery/granular material was about 0 mg/s when the content of titanium oxide is 0 wt %, about 2 mg/s when the content of titanium oxide was 0.5 wt %, about 9 mg/s when the content of titanium oxide was 1 wt %, about 11.2 mg/s when the content of titanium oxide was 5 wt % and about 15 mg/s when the content of titanium oxide was 10 wt %. As a result, PMMA-$TiO_2$ can be understood to increase its flowability as the amount of $TiO_2$ fused to the outer surfaces increases. In this way, the flow rate per unit time of the powdery/granular material flowing in the tube 11 in the case where vibration is given to the tube 11 by the vibrator 2 so that the amplitude of the tube 11 has a specified level can be used as the evaluation value for the flowability of the powdery/granular material. Of course, this evaluation value for the flowability is also a value relating to the compressibility of the powdery/granular material as described above and can be used as an evaluation value for the compressibility if the compressibility of the powdery/granular material is a main viewpoint.

Alternatively, a change of the flow rate per unit time of the powdery/granular material flowing in the tube 11 with time in the case where vibration is given to the tube 11 by the vibrator 2 so that the amplitude of the tube 11 (amplitude of the narrower tube portion 1122 in the vicinity of the flow-out port 1123 in this embodiment) has a specified level may be used as the evaluation value for the flowability of the powdery/granular material.

Figure 6:
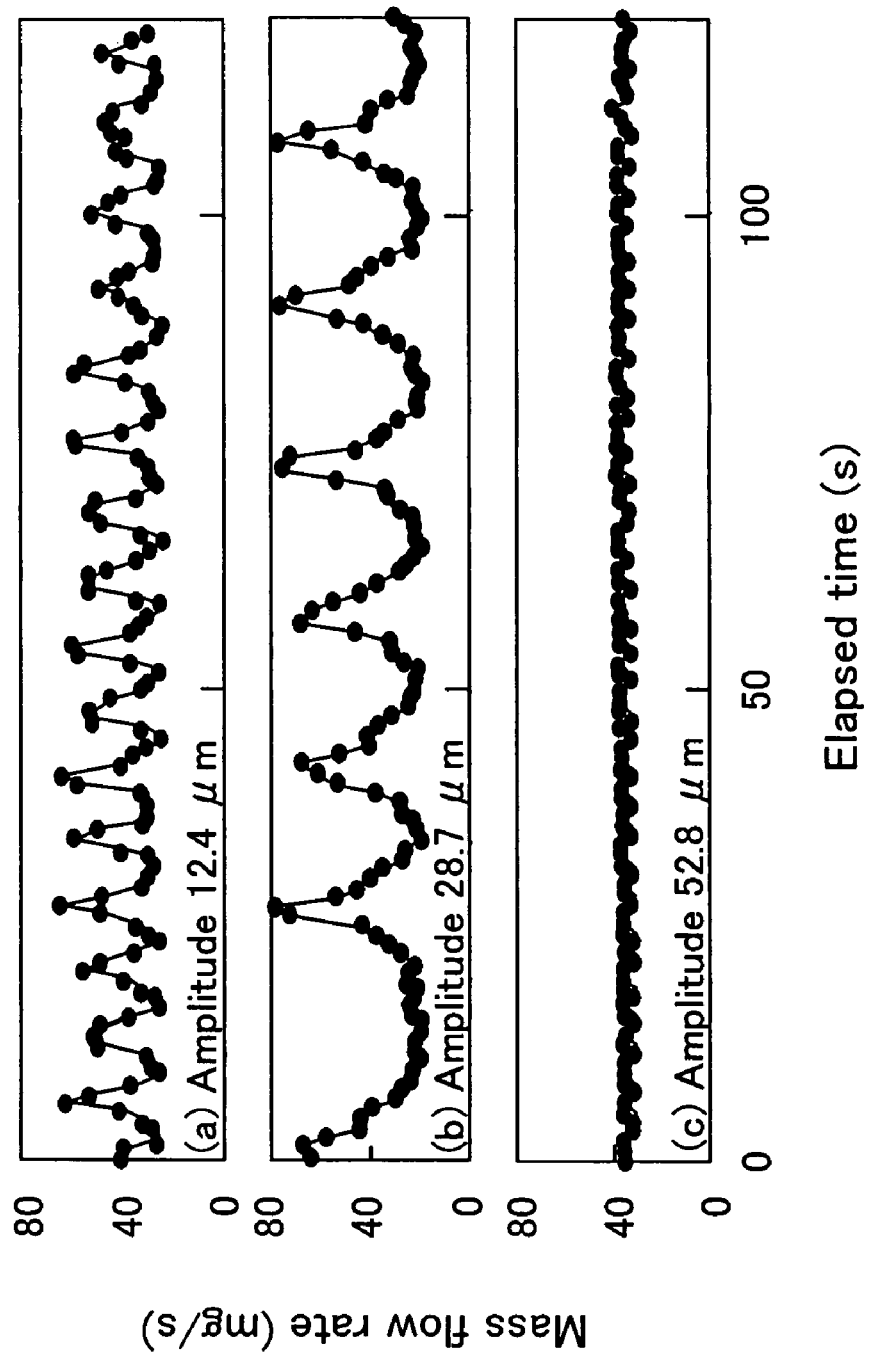

FIG. 6 are graphs showing changes in the flowing rate per unit time of the powdery/granular material with time at specified amplitudes. In FIG. 6, a horizontal axis represents the elapsed time in seconds and a vertical axis represents the flow rate per unit time in mg/s. FIG. 6 show measurement results of PMMA having an average particle diameter of about 58.2 μm in the case of vibration at a frequency of 330 Hz. FIG. 6A shows a case where the amplitude was about 12.4 μm, FIG. 6B shows a case where the amplitude was 28.7 μm and FIG. 6C shows a case where the amplitude was 52.8 μm.

The changes of the flow rate per unit time of the powdery/granular material with time at the specified amplitudes are categorized into cases where the flow rate per unit time of the powdery/granular material repeatedly changes in its magnitude to pulsate as time elapses (pulsated flow) as shown in FIGS. 6A and 6B, cases where the flow rate per unit time of the powdery/granular material is substantially constant without hardly changing as time elapses (constant flow) as shown in FIG. 6C and unillustrated cases where the flow temporarily stops to create the flow like pulses and the powdery/granular material intermittently flows (intermittent flow). The changes of the flow rate per unit time of the powdery/granular material with time at the specified amplitudes depend on the level of the amplitude of the vibration because the flow changes from the pulsated flow to the constant flow as the amplitude increases in the example shown in FIG. 6. Further, even in the pulsated flows, as the amplitude increases, changes in the flow rate per unit time change from a state where amplitudes are smaller to a state where amplitudes are larger and from a state where the frequency is high to a state where the frequency is low.

As described above, the change of the flow rate per unit time of the powdery/granular material flowing in the tube 11 with time in the case where vibration is given to the tube 11 by the vibrator 2 so that the amplitude of the tube 11 has a specified level can be used as the evaluation value for the flowability of the powdery/granular material and, particularly, the stability of the flow can be evaluated depending on the presence or absence of the pulsation, i.e. whether the flow is a pulsated flow or an intermittent flow, or a constant flow.

Although the powdery/granular material flowability evaluation apparatus A is constructed to generate and output the graph of the flow rate per unit time in relation to amplitude in the above embodiment, it may be constructed to measure only the amplitude of the tube 11 when the powdery/granular material fell from the tube 11, calculate and output the evaluation value. Alternatively, the powdery/granular material flowability evaluation apparatus A may be constructed to give vibration to the tube 11 by means of the vibrator 2 so that the amplitude of the tube 11 has a specified level, measure only the flow rate per unit time of the powdery/granular material flowing in the tube 11 in this case, calculate and output the evaluation value.

Further, in the above embodiment, the powdery/granular material flowability evaluation apparatus A is constructed to measure the amplitude of the tube and the weight of the fallen powdery/granular material at each one of the amplitudes of the vibration of the vibrator 2 within the specified range by giving the vibration of a certain amplitude to the tube 11 by means of the vibrator 2 only for a specified time and successively increasing this amplitude at specified intervals of time. However, the powdery/granular material flowability evaluation apparatus A may be constructed to measure the amplitude of the tube and the weight of the fallen powdery/granular material while the amplitude of the vibration given to the tube 11 by means of the vibrator 2 is continuously changed at a specified rate within the specified range. By this construction, the graph of the flow rate per unit time in relation to amplitude can be obtained and the specified evaluation value can be calculated within a shorter period of time. A rate at which the amplitude of the vibration is continuously changed can be suitably set according to the powdery/granular material to be measured.

Alternatively, the powdery/granular material flowability evaluation apparatus A may be constructed as follows in the case where the amplitude of the vibration given to the tube 11 by means of the vibrator 2 is continuously changed at the specified rate within the specified range. A relationship between the amplitude continuously changing at the specified rate and the elapsed time (elapsed time-amplitude relationship) is obtained beforehand. Instead of measuring the amplitude of the tube 11, an elapsed time-amplitude relationship information storage 521 storing information representing the thus obtained elapsed time-amplitude relationship (elapsed time-amplitude relationship information) is functionally provided in the storage device 52 as shown in broken line in FIG. 1, and the evaluation value calculating section 512 calculates the evaluation value evaluating the flowability of the powdery/granular material based on the elapsed time-amplitude relationship stored in the elapsed time-amplitude relationship information storage 521 beforehand and the weight measured by the electric balance 4.

The elapsed time-amplitude relationship is, for example, represented by an arithmetic expression defining a relationship between the elapsed time and the amplitude or a lookup table defining a correspondence between the elapsed time and the amplitude. Further, the evaluation value calculating section 512 calculates the evaluation value of the powdery/granular material, for example, by converting the elapsed time from the start of the measurement to a timing of notification into an amplitude using the elapsed time-amplitude relationship upon receiving the notification of the weight of the powdery/granular material from the electric balance 4 via the interface 53 and obtaining a graph of the flow rate per unit time in relation to amplitude from the weight of the powdery/granular material notified from the electric balance 4 and the converted amplitude.

By this construction as well, the graph of the flow rate per unit time in relation to amplitude can be obtained and the specified evaluation value can be calculated within a shorter period of time.

Figure 7:
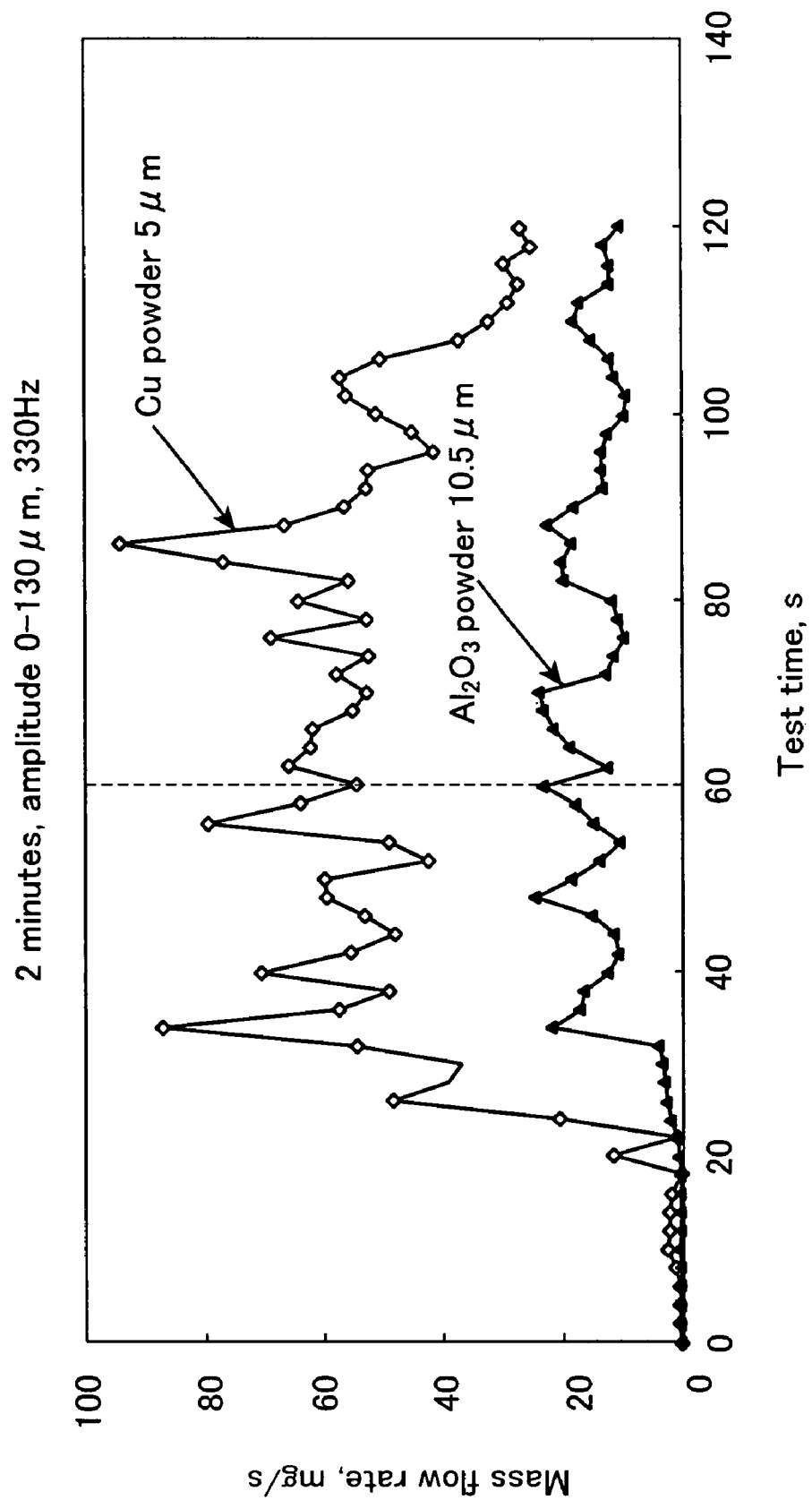
FIG. 7 is a graph showing the flow rate per unit time in relation to the lapse of time.

FIG. 7 is a graph showing a flow rate per unit time in relation to elapsed time. In FIG. 7, a horizontal axis represents time in seconds and a vertical axis represents flow rate in mg/s. Although the horizontal axis represents time in FIG. 7, it also represents amplitude since the amplitude is continuously changed at a specified rate. FIG. 7 shows a measurement result in the case the vibrator 2 is controlled to increase the amplitude of the vibration given to the tube 11 from 0 to 130 μm for two minutes for a copper (Cu) powdery/granular material having an average particle diameter of about 5 μm and an aluminum oxide ($Al_2O_3$) powdery/granular material having an average particle diameter of about 10.5 μm. i.e. a measurement result in the case where the amplitude is continuously increased at a rate of 130/120 μm/s. The frequency of the vibration is 330 Hz. ◇ represents the measurement result of copper and ▲ represents the measurement result of aluminum oxide.

In the example shown in FIG. 7, the evaluation value for copper is about 22.7 μm (=130/120×21) and the one for aluminum oxide is about 32.5 μm (=130/120×30) as can be understood from FIG. 7 if the amplitude of the tube 11 when the powdery/granular material fell from the tube 11 is assumed as the evaluation value for the flowability. If the flow rate per unit time of the powdery/granular material flowing in the tube 11 in the case where the vibration is given to the tube 11 by the vibrator 2 so that the amplitude of the tube 11 has a specified level is assumed as the evaluation value for the flowability, the evaluation value for copper is about 55 mg/s and the evaluation value for aluminum oxide is about 23 mg/s, for example, when the elapse time is 60 sec. (i.e. amplitude is 65 μm). As a result, it can be understood that the copper has higher flowability than aluminum oxide.

Figure 8:
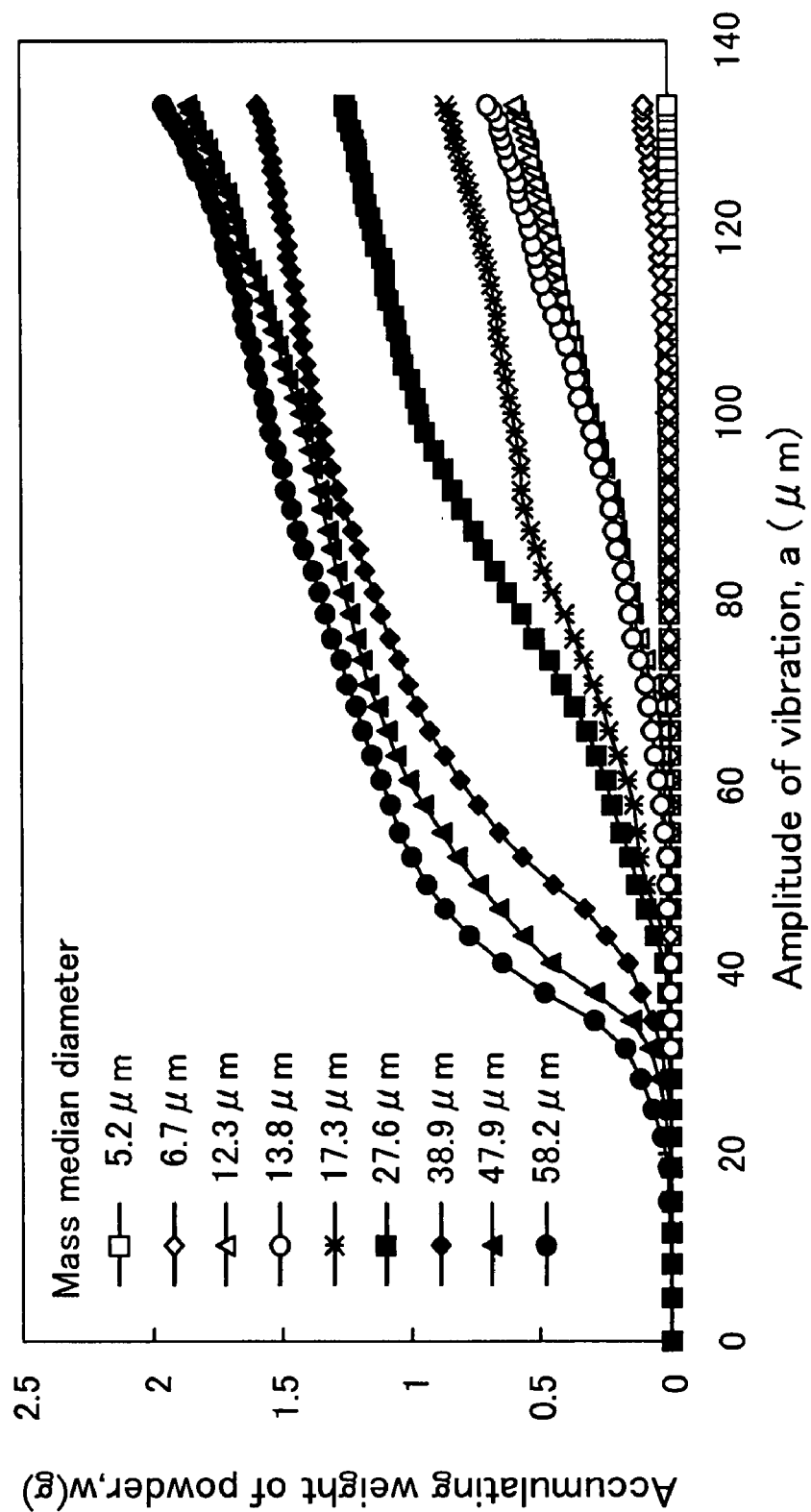
FIG. 8 is a graph according to another example showing the cumulative amounts of the powdery/granular material flowing out from the tube in relation to an amplitude change in the case where the amplitude of vibration is increased to a specified level.

FIG. 8 is a graph showing cumulative amounts of powdery/granular materials flown out from the tube in relation to an amplitude change according to another example. In FIG. 8, a horizontal axis represents amplitude in μm and a vertical axis represent cumulative amount of the powdery/granular material flown out from the tube 11 in g. Although the horizontal axis represents amplitude in μm in FIG. 8, it also represents elapsed time since the amplitude is continuously changed at a specified rate. Further, in FIG. 8, the flow rates per unit time can be obtained as in FIG. 7 by time-differentiating the cumulative amounts of the powdery/granular materials flown out from the tube 11. FIG. 8 shows measurement results in the case of controlling the vibrator 2 to increase the amplitude of the vibration given to the tube 11 from 0 to 130 μm for two minutes for the respective PMMA powdery/granular materials having an average particle diameter of about 5.2 μm (□), about 6.7 μm (◊), about 12.3 μm (Δ), about 13.8 μm (○), about 17.3 μm (*), about 27.6 μm (■), about 38.9 μm (♦), about 47.9 μm (▲) and about 58.2 μm (●). The frequency of the vibration is 330 Hz.

In the example shown in FIG. 8, the evaluation value is smaller as the average particle increases and the fall of the powdery/granular material starts at a smaller amplitude if the amplitude of the tube 11 when the powdery/granular material first fell from the tube 11 is assumed as the evaluation value for the flowability as can be understood from FIG. 8. Further, if the flow rate per unit time of the powdery/granular material flowing in the tube 11 in the case where the vibration is given to the tube 11 by the vibrator 2 so that the amplitude of the tube has a specified level is assumed as the evaluation value for the flowability, it can be understood from the inclinations of the respective characteristic curves shown in FIG. 8 that the evaluation value is larger and the flowability is higher as the average particle diameter increases.

Although the measurements were made by giving the vibration to the tube 11 while the amplitude was continuously changed at the specified rate in FIGS. 4, 7 and 8, they may be made by giving the vibration to the tube 11 while the amplitude is continuously decreased at a specified rate.

In the above embodiment, the powdery/granular material flowability evaluation apparatus A is constructed to measure the amplitude of the tube 11 and the weight of the fallen powdery/granular material at each one of the amplitudes of the vibration of the vibrator 2 within the specified range by giving the vibration of a certain amplitude to the tube 11 by means of the vibrator 2 only for the specified time and successively increasing this amplitude at the specified intervals of time. However, the powdery/granular material flowability evaluation apparatus A may be constructed to measure the amplitude of the tube 11 and the weight of the fallen powdery/granular material while the amplitude of the vibration given to the tube 11 by means of the vibrator 2 is continuously decreased or increased at a specified rate after being continuously increased or decreased at a specified rate up to a preset level. By this construction, the graph of the flow rate per unit time in relation to amplitude can be obtained within a shorter period of time and a hysteresis of the flow rate per unit time in relation to amplitude can be obtained.

Alternatively, the powdery/granular material flowability evaluation apparatus A may be constructed as follows in the case where the amplitude of the vibration given to the tube 11 by means of the vibrator 2 within the specified range is continuously decreased or increased at the specified rate after being continuously increased or decreased at the specified rate up to the preset level. A relationship between the amplitude continuously changing at the specified rate and an elapsed time (elapsed time-amplitude relationship) is obtained beforehand. Instead of measuring the amplitude of the tube 11, an elapsed time-amplitude relationship information storage 521 (shown in broken line in FIG. 1) storing information representing the elapsed time-amplitude relationship (elapsed time-amplitude relationship information) thus obtained beforehand as described above is functionally provided in the storage device 52, and the evaluation value calculating section 512 calculates the evaluation value evaluating the flowability of the powdery/granular material based on the elapsed time-amplitude relationship stored in the elapsed time-amplitude relationship information storage 521 beforehand and the weight measured by the electric balance 4.

By this construction as well, the graph of the flow rate per unit time in relation to amplitude can be obtained within a shorter period of time and a hysteresis of the flow rate per unit time in relation to amplitude can be obtained.

Figure 9:
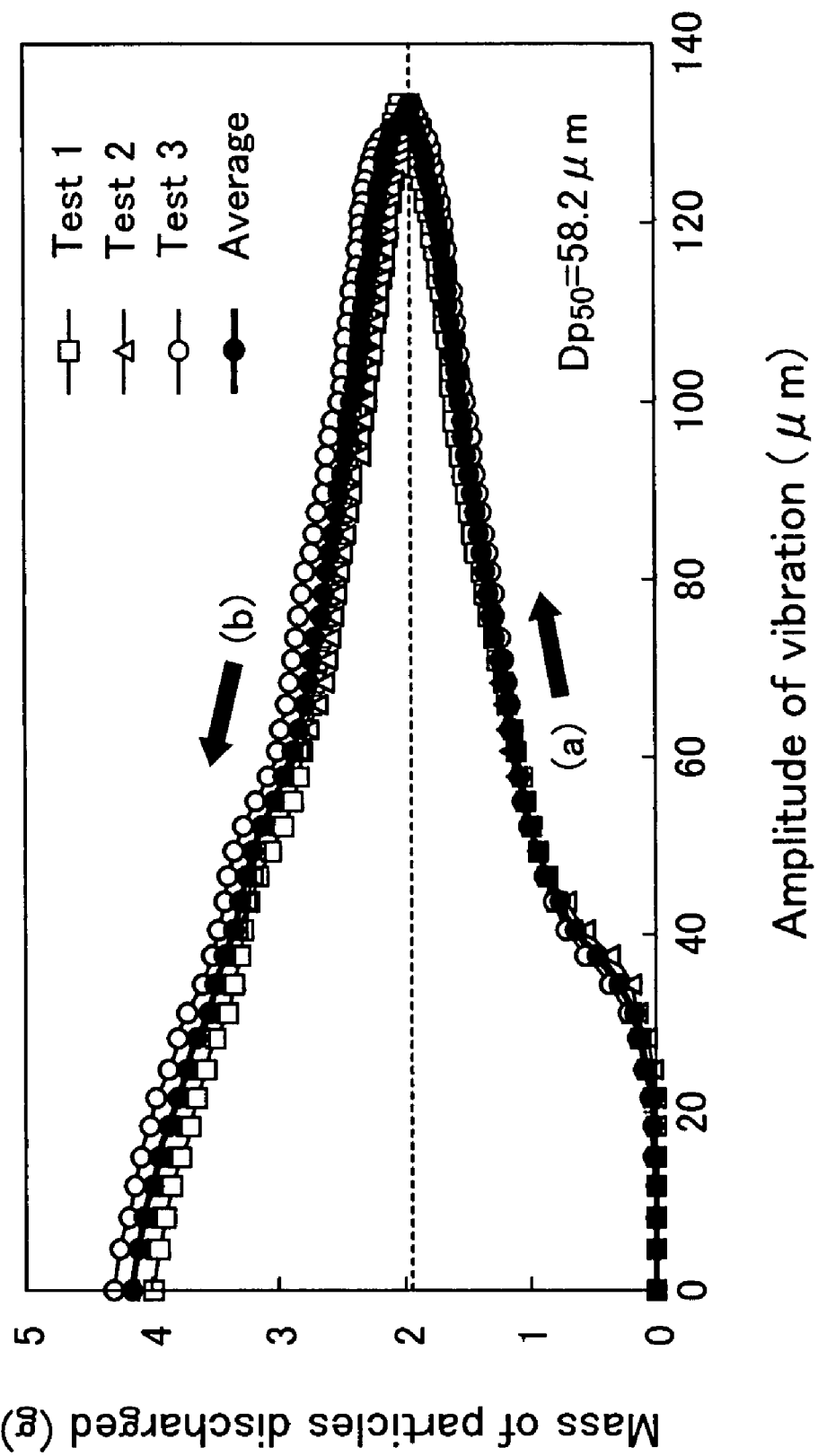
FIG. 9 is a graph showing cumulative amounts of the powdery/granular material flowing out from the tube in relation to an amplitude change in the case of decreasing the amplitude of the vibration after increasing it to a specified level.

FIG. 9 is a graph showing cumulative amounts of powdery/granular materials flown out from the tube in relation to an amplitude change in the case where the amplitude of the vibration is decreased after being increased to a specified level. In FIG. 9, a horizontal axis represents the amplitude in μm and a vertical axis represents the cumulative amount of the powdery/granular material flown out from the tube 11 in g. Although the horizontal axis represents the amplitude in FIG. 9, it also represents an elapsed time since the amplitude is continuously changed at a specified rate. In FIG. 9, the flow rates per unit time can be obtained as in FIG. 7 by time-differentiating the cumulative amounts of the powdery/granular materials flown out from the tube 11. FIG. 9 shows measurement results in the case of controlling the vibrator 2 to decrease the amplitude of the vibration given to the tube 11 for PMMA powdery/granular materials having an average particle diameter of about 58.2 μm from 130 to 0 μm for two minutes after increasing this amplitude from 0 to 130 μm for two minutes. The frequency of the vibrator is 330 Hz. In the example shown in FIG. 9, three measurements are conducted, wherein the first one (Test 1) is shown by □, the second one (Test 2) by Δ and the third one (Test 3) by ○ and an average of these is shown by ●.

As can be understood from FIG. 9, if the amplitude of the vibration given to the tube 11 by the vibrator 2 is continuously decreased at the specified rate after being continuously increased at the specified rate up to the specified level, the change of the cumulative amount of the powdery/granular material flown out from the tube in relation to the amplitude change, i.e. the change of the flow rate per unit time in relation to the amplitude change, differs between the case where the amplitude of the vibration is continuously increased at the specified rate up to the specified level and the case where the amplitude of the vibration is thereafter continuously decreased at the specified rate up to the specified level. Specifically, if the amplitude of the vibration given to the tube 11 by the vibrator 2 is continuously decreased at the specified rate after being continuously increased at the specified rate up to the specified level, the change of the cumulative amount of the powdery/granular material flown out from the tube in relation to the amplitude change (change of the flow rate per unit time in relation to the amplitude change) draws a hysteresis curve. In the example shown in FIG. 9, the change of the cumulative amount of the powdery/granular material flown out from the tube in relation to the amplitude change (change of the flow rate per unit time in relation to the amplitude change) takes on different profiles particularly in the case where the amplitude is increased from 0 to about 60 μm and in the case where the amplitude is decreased from about 60 to 0 μm.

This is because the vibration energy is first consumed to reduce the spaces formed in spots (parts where the density of the powdery/granular material is rough) and the flow of the powdery/granular material starts at a certain amplitude as described above in the case of increasing the amplitude from 0 to 130 μm, but such spaces are already reduced in size and there are hardly no spots hindering the flow of the powdery/granular material in the case of decreasing the amplitude from 130 to 0 μm. Thus, the powdery/granular material does not flow in the case of increasing the amplitude in a range from 0 to 20 μm, whereas the flow can be seen in the case of decreasing the amplitude in a range from 20 to 0 μm.

Such a hysteresis of the change of the flow rate per unit time in relation to the amplitude change can be used as the evaluation value for the flowability of the powdery/granular material and particularly as the evaluation value for the flowability also considering the compressibility of the powdery/granular material.

Although the vibrator 2 includes one vibrator main body 21 for generating vibration and gives vibration to the tube 11 in one direction in a horizontal plane with respect to the longitudinal direction of the tube 11 in the above embodiment, it may include a plurality of vibrator main bodies for generating vibrations and may give vibrations to the tube 11 in different directions in a horizontal plane with respect to the longitudinal direction of the tube 11. In this case, the vibrator 2 includes, for example, a vibrator main body (first vibrator main body) 21 and a second vibrator main body 23 shown in broken line in FIG. 1 for generating the vibrations, and a vibration transmitting member 22 for transmitting the vibrations generated by the first and second vibrator main bodies 21, 23.

Figure 10:
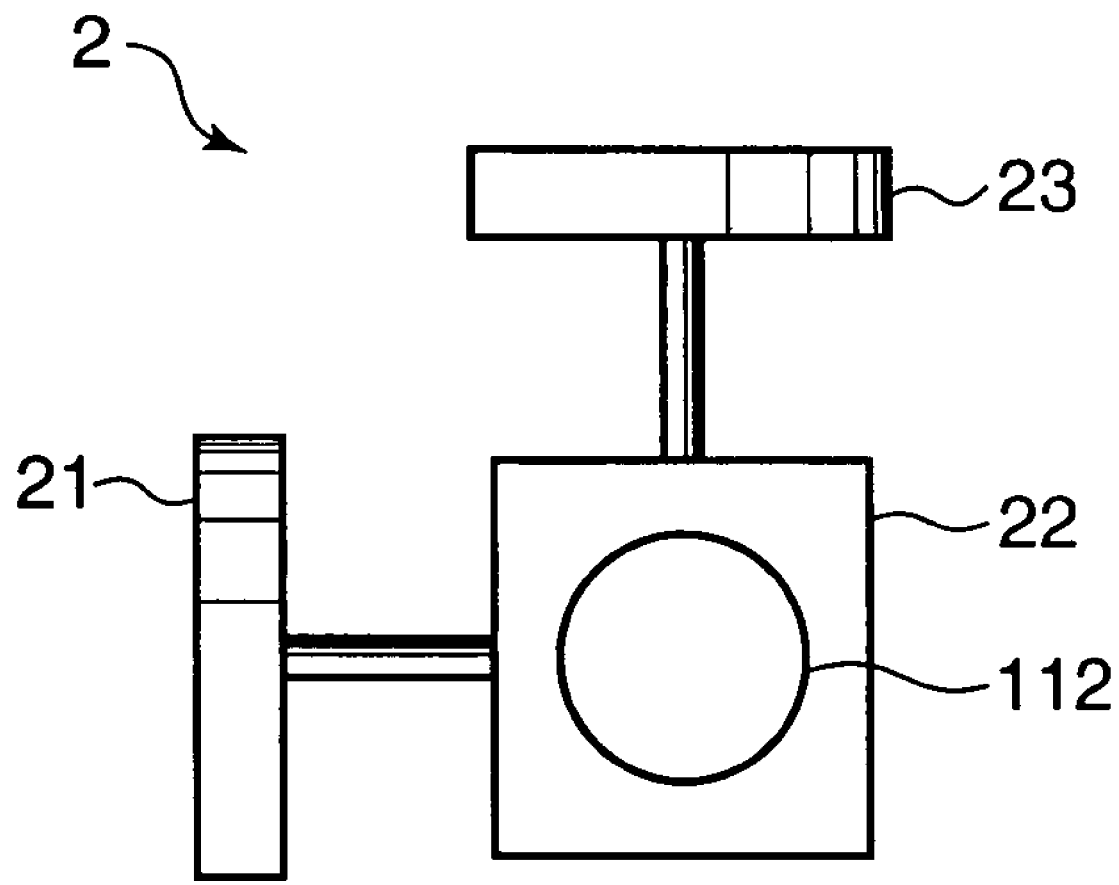
FIG. 10 is a horizontal section along X-X of FIG. 1.

FIG. 10 is a horizontal section along X-X of FIG. 1 showing a state where the first and second vibrator main bodies 21, 23 are attached to the tube 11 via the vibration transmitting member 22. As shown in FIGS. 1 and 10, the first and second vibrator main bodies 21, 23 are so attached to the tube 11 via the vibration transmitting member 22 so that the vibrations are given to the tube 11 in mutually different directions in a horizontal plane with respect to the longitudinal direction of the tube 11. In the example shown in FIGS. 1 and 10, the first and second vibrator main bodies 21, 23 are attached to the tube 11 via the vibration transmitting member 22 so as to give the vibrations to the tube 11 in orthogonal directions.

The first and second vibrator main bodies 21, 23 give the vibrations to the tube 11 via the vibration transmitting member 22 at specified frequency and amplitude in accordance with a control signal from the arithmetic unit 5. The vibrations given to the tube 11 by the first and second vibrator main bodies 21, 23 may have mutually different waveforms.

Figure 11:
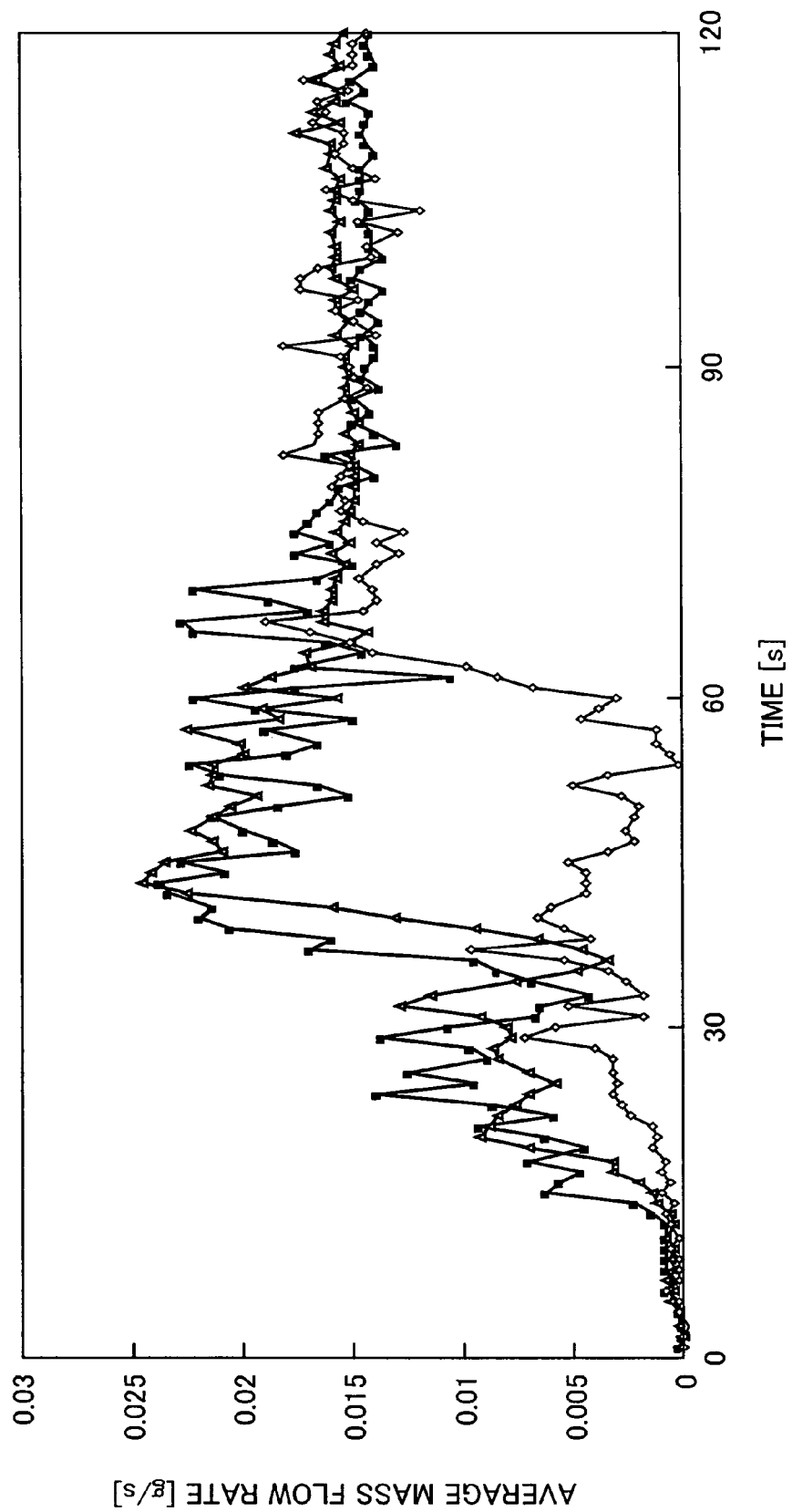
FIG. 11 is a graph showing the flow rate per unit time in relation to the lapse of time in the case where vibrations having different waveforms are given to the tube in two directions.

FIG. 11 is a graph showing a flow rate per unit time in relation to an elapsed time in the case where vibrations having different waveforms are given to the tube in two directions. In FIG. 11, a horizontal axis represents time in seconds and a vertical axis represents a flow rate in g/s. Although the horizontal axis represents the time in FIG. 11, it also represents the amplitude since the amplitude is continuously changed at a specified rate. FIG. 11 shows measurement results for spherical silica having an average particle diameter of about 20 μm. The first vibrator main body 21 gave vibration to the tube 11 to increase the amplitude from 0 to 130 μm for two minutes at a frequency of 330 Hz in any one of the following cases. ■ represents a measurement result in the case where the second vibrator main body 23 gave rectangular wave vibration having an amplitude of 50 μm to the tube 11 at a frequency of 2 Hz. ∆ represents a measurement result in the case where the second vibrator main body 23 gave pulsed vibration having an amplitude of 50 μm to the tube 11 at a frequency of 2 Hz. Further, ◇ represents a measurement result as a reference data in the case where the second vibrator main body 23 gave no vibration to the tube 11.

As can be understood from FIG. 11, if the vibration having a lower frequency than that of the first vibrator main body 21 is given to the tube 11 by the second vibrator main body 23, the value of the amplitude at which the flow of the powdery/granular material starts (flow starting point) in the characteristic curve of the flow rate per unit time in relation to amplitude does not change, but the succeeding flow rate in this characteristic curve is larger as compared to the case where no vibration is given to the tube 11 by the second vibrator main body 23. Thus, in the powdery/granular material flowability evaluation apparatus A having such a construction, hindrance to the flow caused by cross-link formation can be suppressed and such evaluation values among the respective powdery/granular materials to be measured can be obtained within a short period of time.

Although the frequency is relatively low in the above example, a higher frequency or a frequency in the ultrasonic range may be, of course, selected as already described that an ultrasonic vibrator apparatus can be adopted as the vibrator 2.

Although the vibration of the tube 11 is measured by the laser vibrometer 3 in the above embodiment, it may be obtained based on the level of the drive voltage for driving the vibrator main body 21 (23) of the vibrator 2 since the amplitude of the vibrator in the vibrator main body 21 (23) of the vibrator 2 is proportional to the level (magnitude) of the drive voltage for driving the vibrator main body 21 (23). For example, a relationship between the level of the drive voltage and the amplitude of the tube 11 is obtained beforehand, and the amplitude of the tube 11 is obtained from the level of the drive voltage using this relationship. By constructing the powdery/granular material flowability evaluation apparatus A in this way, the amplitude can be measured even if the tube 11 vibrates in the high-frequency range or ultrasonic range.

Alternatively, the powdery/granular material flowability evaluation apparatus A may be constructed such that a piezoelectric element bonded over the entire circumference to the outer circumferential surface of the narrower tube portion 1122 in the vicinity of the flow-out port 1123 of the tube 11 may be used instead of the laser vibrometer 3 to measure the amplitude of the tube 11. The piezoelectric element bonded to the narrower tube portion 1122 is distorted by the vibration of the narrower tube portion 1122 and outputs a voltage corresponding to this distortion. By constructing the powdery/granular material flowability evaluation apparatus A in this way, the amplitude can be measured even if the tube 11 vibrates in the high-frequency range or ultrasonic range.

In this specification are disclosed various inventions as above, out of which main inventions are summarized below.

A powdery/granular material flowability evaluation apparatus according to one aspect of the present invention comprises a storage tank for storing a powdery/granular material to be evaluated; a vertical or inclined tube whose flow-out port is connected with a discharge port of the storage tank through which the powdery/granular material is discharged; a vibrator unit for giving vibration to the tube; an amplitude meter for measuring the amplitude of the tube; a weight meter for measuring the weight of the powdery/granular material fallen through the tube from the storage tank; and an evaluation value calculator for calculating an evaluation value evaluating the flowability of the powdery/granular material based on the amplitude measured by the amplitude meter and the weight measured by the weight meter. A powdery/granular material flowability evaluation method according to another aspect of the present invention comprises the steps of giving vibration to a vertical or inclined tube having a storage tank for storing a powdery/granular material to be measured arranged at one end thereof such that the powdery/granular material flows into the tube from the storage tank; measuring the amplitude of the tube; measuring the weight of the powdery/granular material fallen through the tube from the storage tank; and calculating an evaluation value evaluating the flowability of the powdery/granular material based on the measured amplitude and weight.

According to the above powdery/granular material flowability evaluation apparatus and powdery/granular material flowability evaluation method, the flowability of the powdery/granular material can be evaluated in a dynamic state where the powdery/granular material itself is flowing or is about to start flowing.

In the above powdery/granular material flowability evaluation apparatus, the vibrator unit gives the vibration to the tube while continuously changing the amplitude of the vibration at a specified rate. Further, in the above powdery/granular material flowability evaluation apparatus, the vibrator unit gives the vibration to the tube while continuously changing the amplitude of the vibration at a specified rate; a storage device storing a relationship between the amplitude continuously changing at the specified rate and an elapsed time beforehand is provided instead of the amplitude meter; and the evaluation value calculator calculates the evaluation value evaluating the flowability of the powdery/granular material based on the relationship stored in the storage device and the weight measured by the weight meter. In the powdery/granular material flowability evaluation apparatus having such a construction, a specified evaluation value can be calculated within a shorter period of time.

Further, in the above powdery/granular material flowability evaluation apparatus, a continuous change given by the vibrator unit is a change of decreasing or increasing the amplitude after increasing or decreasing the amplitude up to a specified level. In the powdery/granular material flowability evaluation apparatus having such a construction, a specified evaluation value can be calculated within a shorter period of time. Particularly, a hysteresis of a change of a flow rate per unit time in relation to an amplitude change can be calculated as an evaluation value for the flowability. By dosing so, hystereses of the flows among powdery/granular materials to be measured can be relatively evaluated.

In these above powdery/granular material flowability evaluation apparatuses, the evaluation value is a flow rate per unit time of the powdery/granular material flowing in the tube in the case where vibration is given to the tube by the vibrator unit so that the amplitude of the tube has a specified level. In the powdery/granular material flowability evaluation apparatuses having such a construction, the flow rates of the powdery/granular materials to be measured can be relatively evaluated by such evaluation values.

Further, in these above powdery/granular material flowability evaluation apparatuses, the evaluation value is a change of the flow rate per unit time of the powdery/granular material flowing in the tube with time in the tube in the case where vibration is given to the tube by the vibrator unit so that the amplitude of the tube has a specified level. In the powdery/granular material flowability evaluation apparatuses having such a construction, stabilities and compressibilities, and flowabilities of the powdery/granular materials to be measured can be relatively evaluated by such evaluation values.

Furthermore, in these above powdery/granular material flowability evaluation apparatuses, the evaluation value is the amplitude of the tube when the powdery/granular material first fell from the tube. In the powdery/granular material flowability evaluation apparatuses having such a construction, the flow starting points of the powdery/granular materials to be measured can be relatively evaluated by such evaluation values.

Further, in these above powdery/granular material flowability evaluation apparatuses, the vibrator unit gives vibrations to the tube in mutually different directions in a horizontal plane with respect to the longitudinal direction of the tube. Furthermore, in these above powdery/granular material flowability evaluation apparatuses, the respective vibrations given to the tube in the mutually different directions in the horizontal plane with respect to the longitudinal direction of the tube have waveforms different from each other. In the powdery/granular material flowability evaluation apparatuses having such a construction, hindrance to the flow by cross-link formation can be suppressed. Therefore, the value of the amplitude at which the powdery/granular material starts flowing and a maximum flow rate in a characteristic curve of the flow rate per unit time in relation to amplitude can be measured within a shorter period of time.

Further, in these above powdery/granular material flowability evaluation apparatuses, the vibrator unit includes a piezoelectric element. In the powdery/granular material flowability evaluation apparatuses having such a construction, the amplitude of the vibration can be easily continuously changed while the frequency is fixed at a specified frequency set beforehand since the amplitude and frequency (number of vibration) of the vibration can be independently controlled.

Although the present invention has been suitably and adequately described above by way of the embodiment while referring to the drawings in order to represent the present invention, it should be appreciated that a person skilled in the art can easily modify and/or improve the above embodiment. Accordingly, unless modified or improved embodiment of the person skilled in the art departs from the scope of the right as claimed, such modified or improved embodiment should be understood to be embraced by the scope as claimed.

INDUSTRIAL APPLICABILITY

According to the present invention, there can be provided a powdery/granular material flowability evaluation apparatus and a powdery/granular material flowability evaluation method capable of relatively evaluating the flowability of a powdery/granular material.

The invention claimed is:
1. A powdery/granular material flowability evaluation apparatus comprising:
    a storage tank for storing a powdery/granular material to be evaluated;
    a vertical or inclined tube whose flow-out port is connected with a discharge port of the storage tank through which the powdery/granular material is discharged;
    a vibrator unit for giving vibration to the tube at a predetermined constant frequency;
    an amplitude meter for measuring the amplitude of the tube;
    a weight meter for measuring the weight of the powdery/granular material fallen through the tube from the storage tank; and
    an evaluation value calculator for calculating an evaluation value evaluating the flowability of the powdery/granular material based on the amplitude measured by the amplitude meter and the weight measured by the weight meter.
2. A powdery/granular material flowability evaluation apparatus according to claim 1, wherein the vibrator unit gives the vibration to the tube while continuously changing the amplitude of the vibration.
3. A powdery/granular material flowability evaluation apparatus according to claim 1, wherein:
    the vibrator unit gives the vibration to the tube while continuously changing the amplitude of the vibration;

a storage device storing a relationship between the amplitude continuously changing and an elapsed time beforehand is provided instead of the amplitude meter; and the evaluation value calculator calculates the evaluation value evaluating the flowability of the powdery/granular material based on the relationship stored in the storage device and the weight measured by the weight meter.

4. A powdery/granular material flowability evaluation apparatus according to claim 3, wherein a continuous change given by the vibrator unit is a change of decreasing or increasing the amplitude after increasing or decreasing the amplitude up to a specified level.

5. A powdery/granular material flowability evaluation apparatus according to claim 1, wherein the evaluation value is a flow rate per unit time of the powdery/granular material flowing in the tube in the case where vibration is given to the tube by the vibrator unit so that the amplitude of the tube takes a specified level.

6. A powdery/granular material flowability evaluation apparatus according to claim 1, wherein the evaluation value is a change of the flow rate per unit time of the powdery/granular material flowing in the tube in the tube with time in the case where vibration is given to the tube by the vibrator unit so that the amplitude of the tube takes a specified level.

7. A powdery/granular material flowability evaluation apparatus according to claim 1, wherein the evaluation value is the amplitude of the tube when the powdery/granular material first fell from the tube.

8. A powdery/granular material flowability evaluation apparatus according to claim 1, wherein the vibrator unit gives vibrations to the tube in mutually different directions in a horizontal plane with respect to the longitudinal direction of the tube.

9. A powdery/granular material flowability evaluation apparatus according to claim 1, wherein the respective vibrations given to the tube in the mutually different directions in the horizontal plane with respect to the longitudinal direction of the tube have waveforms different from each other.

10. A powdery/granular material flowability evaluation apparatus according to claim 1, wherein the vibrator unit includes a piezoelectric element.

11. A powdery/granular material flowability evaluation method, comprising the steps of:

giving vibration to a vertical or inclined tube having a storage tank for storing a powdery/granular material to be measured arranged at one end thereof such that the powdery/granular material flows into the tube from the storage tank;

measuring the amplitude of the tube;

measuring the weight of the powdery/granular material fallen through the tube from the storage tank; and calculating an evaluation value evaluating the flowability of the powdery/granular material based on the measured amplitude and weight.

\* \* \* \* \*